(12) United States Patent
Huth et al.

(10) Patent No.: US 8,657,447 B2
(45) Date of Patent: Feb. 25, 2014

(54) METHODS AND DEVICES FOR MEASURING TEAR FILM AND DIAGNOSING TEAR DISORDERS

(71) Applicant: Abbott Medical Optics Inc., Santa Ana, CA (US)

(72) Inventors: Stanley W Huth, Newport Beach, CA (US); Denise Tran, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 13/755,295

(22) Filed: Jan. 31, 2013

(65) Prior Publication Data

US 2013/0208246 A1    Aug. 15, 2013

Related U.S. Application Data

(62) Division of application No. 12/962,396, filed on Dec. 7, 2010, now Pat. No. 8,388,136, which is a division of application No. 12/115,350, filed on May 5, 2008, now Pat. No. 7,963,655.

(60) Provisional application No. 60/916,267, filed on May 4, 2007.

(51) Int. Cl.
*A61B 3/00*    (2006.01)

(52) U.S. Cl.
USPC ....................................................... 351/246

(58) Field of Classification Search
USPC ........... 351/246, 221, 205, 200, 209; 356/503
See application file for complete search history.

(56) References Cited

U.S. PATENT DOCUMENTS

| | | | |
|---|---|---|---|
| 6,236,459 B1 | 5/2001 | Negahdaripour et al. | |
| 6,916,096 B2 * | 7/2005 | Eberl et al. | 351/209 |
| 7,281,801 B2 | 10/2007 | Wang | |
| 7,758,190 B2 | 7/2010 | Korb et al. | |
| 7,866,819 B2 | 1/2011 | Tuan | |
| 2004/0212781 A1 | 10/2004 | Mihashi et al. | |
| 2006/0109423 A1 | 5/2006 | Wang | |

OTHER PUBLICATIONS

Fogt N., et al., "Interferometric Measurement of Tear Film Thickness by Use of Spectral Oscillations," Journal of Optical Society of America, 1998, vol. 15 (1), pp. 268-275.

Gardner et al., "Tear Film Thickness: Responsiveness to Potential Cognitive Demands", American Academy of Optometry, Tampa Dec. 2004, 1 page.

Geldis et al., "The Impact of Punctual Occlusion on Soft Contact Lends Wearing Comfort and the Tear Film," Eye and Contact Lens, pp. 261-265, 2008, vol. 34 (5).

(Continued)

*Primary Examiner* — Hung Dang
(74) *Attorney, Agent, or Firm* — Abbott Medical Optics Inc.

(57) ABSTRACT

Methods and devices measure eye blinks and tear film lipid and aqueous layer thickness before and following ophthalmic formula application onto the ocular surface, especially wherein the ophthalmic formula is an artificial tear. The methods and devices are suitable for dry eye diagnosis. The methods and devices are suitable for use to evaluate ophthalmic formula effects on the tear film and to use such information to diagnose ophthalmic formula treatment of ocular disease conditions such as dry eye in the absence of contact lens wear or post-surgical eye drop treatment and diagnosis. The methods and devices are also suitable for use in the optimization of ophthalmic drug dosage forms and sustained drug release.

11 Claims, 10 Drawing Sheets a schematic view of the utility of the present invention.

(56) References Cited

OTHER PUBLICATIONS

Hinel E., et al., "Concurrent interferometric Measures of Lipid Layer Thickness and Tear Film Thinning Before and After Application of Lipid Emulsion Drop", American Academy of Optometry, Anaheim Oct. 2008, 1 page.
International Preliminary Report on Patentability and Written Opinion for Application No. PCT/US08/062682, mailed on Nov. 10, 2009, 12 pages.
International Search Report for Application No. PCT/US08/062682, mailed on Nov. 5, 2008, 6 pages.
Kimball et al., Evaporation is the Primary Mechanism of Pre-Corneal Tear Film Thinning. [online], Oct. 2008 [retieved on Feb. 25, 2009]. Retrieved from the Internet:< URL: http://www.aaopt.org/Submission/Search/SubmissionViewer.asp"SID=2>.
Kimball et al., Improving Interferometric Tear Thickness Measurements by Using Longer Wavelengths. [online], [retrieved on Feb. 25, 2009]. Retrieved from the Internet:< URL: http://www.aaopt.org/Submission/Search/SubmissionViewer.asp"SID=7>.
King S., et al., "Three Interferometric Methods for Measuring the Thickness of Layers of the Tear Film," Optometry and Vision Science, 1999, vol. 76 (1), pp. 19-32.
King S., et al., "Why does Dry Eye Affect Inferior Cornea More than Superior Cornea", American Academy of Optometry, 2002, pp. 1-2.
King-Smith et al., "In vivo Measurement of the Thickness of Human Corneal Endothelium and Descemets Membrane Using Interferometry, E-Abstract 157," Investigative Ophthalmology & Visual Science, 2002, vol. 43.
King-Smith. et. al., "Noninvasive Measurement of the Thickness of the Human Corneal Endothelium and Descemet's Membrane", American Academy of Optometry, Dec. 8, 2001, pp. 1-2.
King-Smith et al., "Roughness of the Corneal Surface by Interferometry", Association for Research in Vision and Ophthalmology, May 6, 2007, 1 page.
King-Smith et al., "The Thickness of the Human Precorneal Tear Film: Evidence from Reflection Spectra," Investigative & Visual Science, pp. 3348-3359, 2000, vol. 41 (11).
King-Smith et al., "The Thickness of the Tear Film," Current Eye Research, pp. 357-368, 2004, vol. 29 (4-5), Taylor & Francis Health Sciences.
King-Smith P., et al., Interferometric Analysis of Reflections from the Tear Film and Ocular Surface. [online], [retrieved on Feb. 25, 2009]. Retrieved from the Internet:< URL: http://www.aaopt.org/Submission/Search/SubmissionViewer.asp"SID=4>.
King-Smith P., et al., "Measurement of the Thickness of the Lipid Layer of the Tear Film Using Reflection Spectra," Association for Research in Vision and Ophthalmology, Inc., 2008, Grand Floridian A, Program 1540.
King-Smith P.E., et al., "A Tear Layer of Thickness 1.6 to 7.3 Micrometer Determined from Reflectance Spectra," Investigative Ophthalmology & Visual Science, 1998, vol. 39 (4), pp. 2446-B303.
King-Smith P.E., et al., "Can the Mucus Layer of the Tear Film be Deomstrated by Interferometry", Investigative Ophthalmology & Visual Science, 2004, vol. 45, pp. 1-2.
King-Smith P.E., et al., "Further Evidence that the Thickness of the Normal Human Tear Film is about 3 Micrometre," Investigative Ophthalmology & Visual Science, 2000, vol. 41 (4), pp. 337-B337.
King-Smith P.E., et al., "Interferometric Imaging of the Full Thickness of the Precorneal Tear Film," Journal of the Optical Society of America A, Optics, Image Science, and Vision, 2006, vol. 23 (9), pp. 2097-2104.
King-Smith P.E., et al., "Is the Thickness of the Tear Film About 40 Micrometre or About 3 Micrometre", Investigative Ophthalmology & Visual Science, 1999, vol. 40 (4), pp. 2876-B751.
King-Smith P.E., et al., "Measurement of Tear Film Thickness by Spectro-Photometry," Investigative Ophthalmology & Visual Science, 1996, vol. 37 (3), pp. 4984-B594.
King-Smith P.,et al., "Is Inferior Tear Film Thinner than Superior Tear Film", Investigative Ophthalmology & Visual Science, 2003, vol. 44, pp. 2476.
Korb D.R., et al., "Tear Film Lipid Layer Thickness as a Function of Blinking," Cornea, 1994, vol. 13 (4), pp. 354-359.
Korb D.R., et al., "The Effect of Two Novel Lubricant Eye Drops on Tear Film Lipid Layer Thickness in Subjects With Dry Eye Symptoms," Optometry and Vision Science, 2005, vol. 82 (7), pp. 494-601.
Nichols, et al., "Assessing Visual Parameters in Dry Eye Disease," Cornea and Contact Lens, [retrieved on Feb. 25, 2009]. Retrieved from the Internet:< URL: http://www.aaopt.org/Submissions.Search/SubmissionViewer.asp"SID=2>.
Nichols et al., "Lipid Layer Thickness and Tear Film Thinning Before and After Application of a Lipid Emulsion Drop,," Association for Research in Vision and Ophthalmoogy, 2008.
Nichols et al., "Tear Film Thickness and Thinning Rate Following a Six-Week Trial of 2% Diquafosol Tetrasodium vs. Placebo in Dry Eye Patients," 2006.
Nichols et al., "The Impact of Contact Lens Care Solutions on the Thickness of the Tear Film and Contact Lens," Cornea, Clinical Sciences, pp. 825-832, 2005, vol. 24 (7).
Nichols J.J., et al., "Hydrogel Contact Lens Binding Induced by Contact Lens Rewetting Drops," Optometry and Vision Science, 2008, vol. 85(4), pp. 236-240.
Nichols J.J., et al., "Thickness of the Pre- and Post-Contact Lens Tear Film Measured in Vivo by Interferometry," Investigative Ophthalmology & Visual Science, 2003, vol. 44 (1), pp. 68-77.
Nichols J.J., et al., "Thinning Rate of the Precorneal and Prelens Tear Films," Investigative Ophthalmology & Visual Science, 2005, vol. 46 (7), pp. 2353-2361.
Nicols et al, "Role of Lipid Layer as a Barrier to Pre-Lens Tear Film Thinning", American Academy of Optometry, Anaheim Oct. 25, 2008, 1 page.
Schlote T., et al., "Marked Reduction and Distinct Patterns of Eye Blinking in Patients With Moderately Dry Eyes During Video Display Terminal Use," Graefe's Archive for Clinical and Experimental Ophthalmology, 2004, vol. 242 (4), pp. 306-312.
Yap M., "Tear Break-up Time is Related to Blink Frequency," Acta Ophthalmologica, 1991, vol. 69 (1), pp. 92-94.
Zhu H., et al., "A Mathematical Model for Ocular Tear and Solute Balance," Current Eye Research, 2005, vol. 30 (10), pp. 841-854.

\* cited by examiner

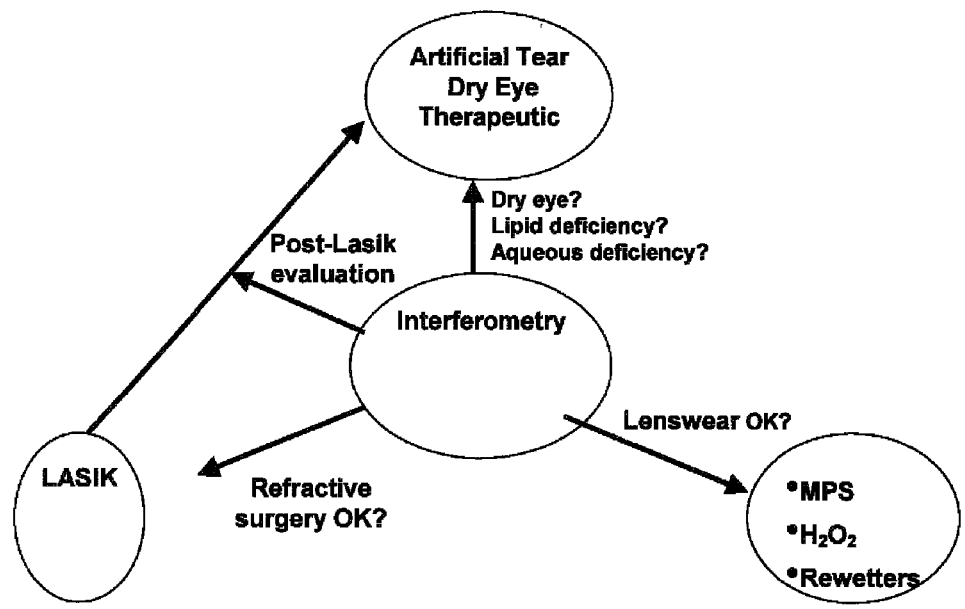
Figure 1: a schematic view of the utility of the present invention.
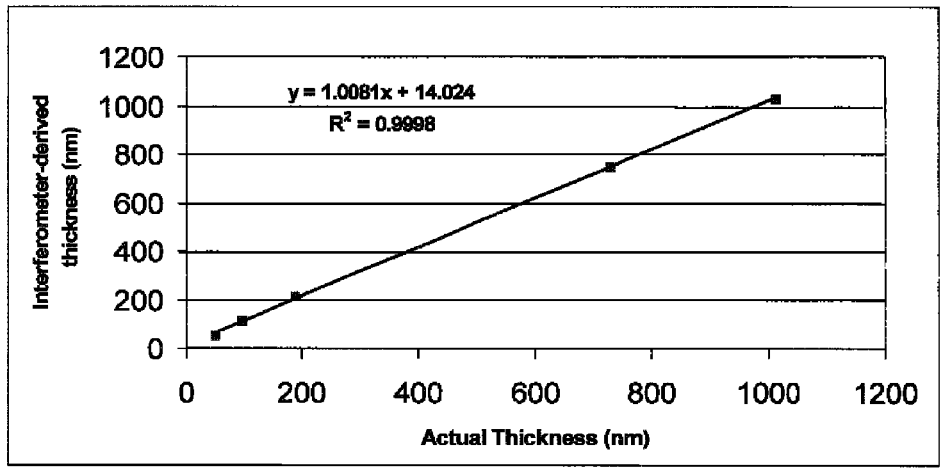
Figure 2. Standard curve from $SiO_2$ thin film thickness standards.

Fourier-Transform-frequency plot of %R vs. time plot from Figure 16

METHODS AND DEVICES FOR MEASURING TEAR FILM AND DIAGNOSING TEAR DISORDERS

This application is a divisional application and claims priority to U.S. application Ser. No. 12/962,396, entitled Methods and Devices for Measuring Tear Film and Diagnosing Tear Disorders, filed Dec. 7, 2010, now U.S. Pat. No. 8,388,136, which is a divisional of U.S. application Ser. No. 12/115,350, filed on May 5, 2008, now U.S. Pat. No. 7,963,655, and claims the benefit of U.S. provisional patent application No. 60/916,267, filed May 4, 2007, the entire contents of which are all hereby incorporated by reference in the entirety for all purposes as if fully set forth herein.

BACKGROUND OF THE INVENTION

1. Field of the Invention

Embodiments of the invention relate to methods and devices for use in evaluating ophthalmic formula effects on the tear film and to use such information to diagnose ophthalmic formula treatment of ocular disease conditions such as dry eye or post-surgical ophthalmic formula treatment and diagnosis.

2. Description of the Related Art

Dry eye syndrome is a prevalent condition among both men and women for which there is no cure, although symptoms may be relieved with proper diagnosis and treatment. The condition affects more than 3.2 million American women middle-aged and older alone (Schaumberg D A, Sullivan D A, Buring J E, Dana M R. Prevalence of dry eye syndrome among US women. *Am J Ophthalmol* 2003 August; 136(2):318-26). Most dry eye patients are prescribed artificial tears to treat their dry eye conditions. Contact lens wearers, computer users, patients who live and/or work in dry environments, and patients with autoimmune disease are all particularly susceptible to developing dry eye.

Individuals with moderate to severe dry eye are unsuitable for contact lens wear and must wear eyeglasses or undergo refractive surgery for their vision correction needs. LASIK refractive surgery induces some degree of dry eye in virtually all patients for a period of time, sometimes six months or more. Cataract surgery also induces some degree of dry eye in a substantial number of patients for a period of time. It may be desirable to prescribe artificial tears for LASIK and cataract surgery patients to treat their dry eye condition.

Current methods for diagnosing dry eye in the absence of contact lens wear utilize methods such as symptom assessment, fluorescein staining, tear film break-up time (TBUT), non-invasive tear film break-up time (NITBUT), Schirmer test, Phenol red thread test, rose bengal or lissamine green staining, conjunctival hyperemia, tear film osmolarity, tear lactoferrin, impression cytology, brush cytology, "tear assessment", blink frequency and maximum interblink interval. For various reasons, all of these methods are imperfect and lacking in precision.

Symptom assessment is most often used for dry eye diagnosis, in the absence or presence of contact lens wear. It is a subjective and qualitative assessment, but was nonetheless used in 82.8% of all diagnoses of dry eye in a recent study (Nichols K K, Nichols J J, Zadnik K. Frequency of dry eye diagnostic test procedures used in various modes of ophthalmic practice. *Cornea* 2000 July; 19(4):477-82).

Fluorescein staining of the cornea is frequently used for dry eye diagnosis, being used in 55.5% of all diagnoses in a recent study (IBID). This is a semi-quantitative assessment which typically consists of dividing the cornea into 5 sections and assessing staining intensity on a 5-point scale. Most fluorescein staining methods also include an assessment of % surface area of staining within each corneal section after the instillation of fluorescein dye into the eye.

Tear film break-up time (TBUT) is another test which is relatively frequently used for dry eye diagnosis, with or without contact lens wear. It was used in 40.7% of all diagnoses of dry eye in a recent study (IBID). The tear film is a continuous film covering the eye. However, it is unstable and breaks up after a short period of time. In patients with dry eyes, the tear film breaks up faster. TBUT measurements are facilitated with the use of fluorescein instilled into the eye with the use of a fluorescein strip. However, the instillation of fluorescein often stimulates reflex tearing, obviating the measurement of TBUT. Also, the presence of fluorescein in the tear film changes the properties of tears, which means that the measurements may not be truly physiological. TBUT measurements are also not precise.

The non-invasive tear film break-up time (NITBUT) method was developed to overcome the limitations of the TBUT method. With the NITBUT method, the eye is observed with a keratometer, hand-held keratoscope or tearscope. The reflections of keratometer mires are observed and the time is measured for a mire to break up following a blink. There is nonetheless considerable variation of NITBUT measurements. Furthermore, tear breakup time is abnormal in many different dry eye states and thus cannot easily differentiate between dry eye types.

The Schirmer test measures the amount of aqueous tears that can be produced by the eye in 5 minutes. If too little aqueous tears are produced, this is indicative of an aqueous deficient dry eye. If enough tears are produced, but symptoms of dry eye exist, this is indicative of an evaporative dry eye for example due to a lipid deficiency, blepharitis or Rosacea. In the Schirmer test, a 35 mm×5 mm filter paper strip is placed into the lower cul-de-sac of the eye and allowed to wet over its length over 5 minutes. Schirmer tests are performed without and with prior application of an anesthetic eyedrop. When an anesthetic eyedrop is not used, the test is considered to measure basal+reflex tear secretion. When an anesthetic eyedrop is used, the test is considered to measure only basal tear secretion. Most clinicians regard the Schirmer test as unduly invasive and of little value for the diagnosis of mild to moderate dry eyes. The test cannot properly diagnose lipid deficient dry eyes. The Schirmer test cannot properly diagnose dry eye states wherein sufficient or even excess aqueous tears are produced. The test, with or without prior use of an anesthetic eyedrop, is also considered to lack precision and accuracy. There is considerable overlap in Schirmer test values between patients with Keratoconjunctivitis sicca (dry eye) and normals.

The Phenol red thread test was developed as a less invasive method than the Schirmer test. It involves the use of a cotton thread impregnated with phenol red dye. The dye changes color from yellow to red when contacted by aqueous tears. The crimped end of a 70 mm long thread is placed in the conjunctival fornix. After 15 seconds, the length of the color change in the thread is measured in millimeters. This test is also nonetheless still invasive and lacks sufficient precision and utility for mild to moderate dry eye diagnosis.

Rose Bengal staining is infrequently used as a dry eye diagnostic. The test involves the instillation of rose bengal dye into the eye and then performing a visual assessment of conjunctival staining. Rose Bengal staining is dependent upon secondary changes in the ocular surface caused by the primary changes due to dry eye and is a good parameter for aqueous tear deficiency only in the absence of other ocular surface diseases.

Conjunctival hyperemia is a subjective assessment of ocular redness. Since redness occurs in ocular conditions other than dry eye (e.g., during infection), this test is unsuitable as an independent diagnostic for dry eye.

Osmolarity, lactoferrin, impression cytology and brush cytology diagnostic methods all involve substantial chemical laboratory work and are thus not suited for general clinical use. Osmolarity cannot independently diagnose dry eye conditions wherein sufficient or even excess aqueous tears are produced.

Tear assessment includes an assessment of total aqueous tear fluid volume via an assessment of inferior tear meniscus height, inferior tear meniscus radius of curvature or meniscus area. Since this method does not evaluate the tear film lipid layer, it is not accurately diagnostic for tear lipid deficiencies, which account for 60% or more of dry eye cases. Tear assessment also includes an evaluation of the tear film lipid layer using a "tearscope". Tearscope-based diagnoses exclude an assessment of the aqueous fluid volume and thus are limited. Additionally, the Keeler tearscope allows only a semi-quantitative analysis of the tear lipid layer, since a spectrum-color analysis of its light source has not been conducted, allowing a correlation between observed colors and thicknesses. Also, colors are still subjectively evaluated.

Blink frequency and maximum interblink interval ($IBI_{max}$) have been determined to correlate to dry eye status. However, both blink frequency and maximum interblink interval measurements have not been routinely used to diagnose dry eye due to the inherent complexity of their measurement, involving video recording and video frame analysis.

Several methods have been employed for measuring the ocular retention times of ophthalmic formulations such as artificial tears used to treat dry eye. Sodium fluorescein has been added to an ophthalmic formulation and the fluorescence signal has been monitored with time using a slit lamp fluorophotometer. This method suffers from at least two problems: first, the fluorescein washes out of the eye at a rate different from that of the formulation components of interest and secondly it diffuses into the ocular tissue. The latter creates a source of error in formulation retention time measurements as it is difficult to distinguish between fluorescence of the thin film from fluorescence from the tissue.

Other methods for measuring the retention times of ophthalmic formulations in the eye include gamma scintigraphy. However, these methods involve the use of radioisotopes and therefore necessitate expensive equipment and a laboratory suited for the handling of isotopes. Also, the radioactive compounds typically have low molecular weights so they too may freely diffuse out of the viscous vehicle and into ocular tissue or be deposited on the lid margins that will result in erroneous retention measurements.

U.S. Pat. No. 5,634,458 discloses a method for determining precorneal retention time of ophthalmic formulations employing a high-molecular weight fluorescein molecule, to avoid tissue uptake of fluorescein. While this method tracks the fluorescence of the high molecular weight fluorescein to obtain a more reliable retention time, it does not measure tear film aqueous or aqueous+lipid layer thickness.

In the context of conducting research on the layers of the tear film, three general methods for measuring tear film layer thickness using optical interference have been developed, corresponding to varying one of three parameters, wavelength of light, angle of incident light and layer thickness, while keeping the other two parameters constant. These optical interferometry methods produce varying light reflection intensity profiles that have been called wavelength-dependent fringes, angle-dependent fringes and thickness-dependent fringes. Thickness-dependent fringes form the basis of the Keeler and Kowa DR-1 instruments. Wavelength-dependent fringes arise from the illumination of the tear film with a measurement beam of light of varying wavelength that intersects with a surface area of the tear film at a constant normal or near-normal angle of incidence. Provided that the tear film has an index of refraction, n, intermediate between that of the surrounding materials, e.g., air on one side and the cornea or a contact lens on the other side, and also that the refractive indices of the adjacent layers or materials are sufficiently different from one another, then the incident light wave will reflect from each boundary between layers or materials of differing refractive index. Multiple reflections will be produced, which will give rise to oscillations in the intensity of the total reflected light as a function of wavelength according to the constructive and destructive interference of the multiple reflected waves, the latter which is dependent upon the relationship between the tear film thickness, d, and the wavelength of light, $\lambda$. Maxima (peaks or fringes) in the reflectance spectrum represents the wavelengths at which constructive interference occurs between light waves reflecting at the front and back surfaces of a thin film and the minima (valleys) represent the wavelengths at which destructive interference occurs between light waves reflecting at the front and back surfaces of a thin film.

In recent years, wavelength-dependent optical interferometers have been developed for in-vivo aqueous tear film and contact lens thickness analysis by King-Smith et al., as disclosed in Fogt N and King-Smith P, Interferometric measurement of tear film thickness by use of spectral oscillations, *J. Opt. Soc. Am. A/Vol.* 15, No. 1/January 1998: 268-275; King-Smith P et al., The Thickness of the Human Precorneal Tear Film: Evidence from Reflection Spectra, *IOVS*, October 2000, Vol. 41, No. 11: 3348-3359 and Nichols J and King-Smith P, Thickness of the Pre- and Post-Contact Lens Tear Film Measured in Vivo by Interferometry, *IOVS*, January 2003, Vol. 44, No. 1: 68-77.

The instruments described in the aforementioned publications are of similar design and are capable of measuring the thickness of the pre-corneal or pre-lens tear film aqueous+lipid layer thickness, post-lens tear film aqueous thickness among contact lens wearers, contact lens thickness and corneal epithelial thickness. The instruments can also measure the thinning or thickening rates of the various tear film layers during normal blinking and between blinks or over time. The instruments have a high degree of quantitative accuracy and precision. However, it is reported in the January 2003 IOVS reference that the interferometer in that reference, the best of the three systems in the aforementioned three references, cannot measure mean thicknesses of less than 1 micron, meaning it cannot measure the tear lipid layer. Tear lipid layer thickness needs to be measured separately in order to determine aqueous-only layer thickness, as the light reflections from the ocular surface arise separately from the combined aqueous+lipid layer and the lipid layer alone. Wavelength-dependent fringes cannot be observed from the aqueous layer only. Lipid layer thickness would have to be measured and subtracted from the combined aqueous+lipid thickness to derive aqueous-only layer thickness. Thus, the aforementioned teaching and instruments measure thicknesses of combined aqueous+lipid layers. Since lipid layer thickness is typically only 2% of the thickness of the aqueous layer (e.g., 60 nm vs. 3000 nm), this only limits the lipid layer diagnostic capability of these instruments. The first interferometer described in the Fogt et al. 1998 reference uses a wavelength range of 369-810 nm. The second two interferometers, described in the IOVS, October 2000 reference and the January 2003 IOVS reference, utilize a wavelength range of 562-1030 nm. The instruments in the aforementioned three references are limited to measuring thickness at a single spot on the eye, approximately 300 microns round, 33×350 microns rectangular or 33×35 microns rectangular in the above three references, respectively, all at the central corneal apex. All of the aforementioned interferometers are capable of kinetic measurements of total tear film layer thickness, to produce thinning or thickening rates as well as measurements of the changes in tear film thickness over time.

Despite the optical interferometer instrument capabilities disclosed in the prior art, the effects of an ophthalmic formula topically applied directly onto the ocular surface on aqueous or aqueous+lipid or lipid tear film thickness have not been fully determined. None of the three aforementioned interferometry publications discloses measurements of tear film thickness over time following the application of an ophthalmic formula directly onto the ocular surface.

Optical coherence tomography (OCT) has most recently been used to measure changes in total tear film thickness (e.g., aqueous+lipid layer thickness) following instillation of artificial tears. 12 mm×2 mm scans of the tear film and cornea were taken at 1310±60 nm at baseline and after instillation of 35 µL of artificial tears (Refresh Liquigel™, Allergan, Irvine, Calif.). Measurements were taken at 5, 20, 40 and 60 minutes after instillation. The authors tested 40 eyes in 20 subjects and found tear film thickening in all subjects, lasting about 60 minutes. Direct measurements of the tear film were not possible, thus total tear film thickness was calculated from the subtraction of the total tear film+cornea thickness at baseline from that after instillation of the artificial tears. OCT instrument repeatability for corneal thickness was reported to be 1.5 µm. Instrument optical error was 3.7 µm, which was larger than the thickness of the normal tear film itself. Thus, this method and instrument also suffers from limited observation capabilities. Observation and measurement of changes in the aqueous or aqueous+lipid or lipid tear film layers from baseline following ophthalmic formula application are important as these allow one to measure important changes in the tear film which likely correlate to ocular surface health status, subjective comfort, optimization of ophthalmic dosage forms and drug delivery.

Given the above limitations of prior art methods for evaluation of the tear film, either alone or before and following ophthalmic formula application, it would be advantageous to have new methods which do not have some or all of the aforementioned limitations.

BRIEF DESCRIPTION OF THE FIGURES

The present invention will now be described in conjunction with the following figures, in which:

FIG. 1 provides a schematic view of the utility of the present invention;

FIG. 2 shows a thickness measurement standard curve using NIST-calibrated thin film thickness standards made from vapor-deposited SiO2 on silicon wafers;

DETAILED DESCRIPTION OF THE PREFERRED EMBODIMENT

Figure 3:
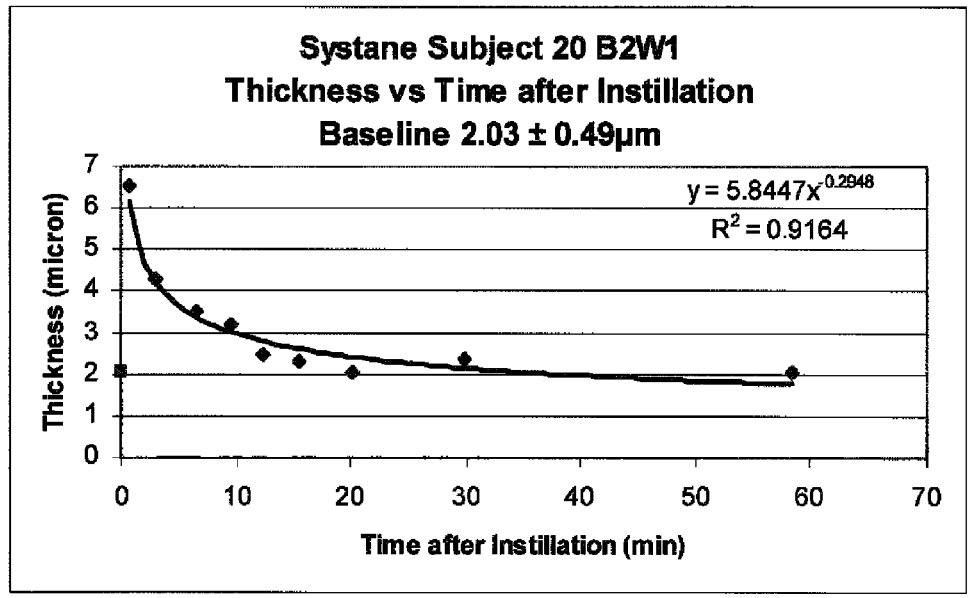
FIG. 3 provides a graph showing a plot of thickness versus time for the aqueous+lipid layers of an eye treated with Systane drops.

The present invention provides an improved device and method for evaluating a patient's tear film. With one instrument, a practitioner will be able to accurately diagnose dry-eye, and whether it is caused by a lipid deficiency or an aqueous deficiency. Based on the results of the tear film analysis, a practitioner will also be able to select an ophthalmic formulation which is specifically formulated to treat the diagnosed condition. For example, in the case of an aqueous deficiency, the practitioner could recommend an artificial tear product which is specifically formulated to supplement the aqueous layer. Similarly, a product which has been formulated to supplement the lipid layer may be recommended in the case of a lipid deficiency. The practitioner will also be able to determine if a patient is a good candidate for LASIK surgery, and whether the LASIK patient will require an artificial tear or dry eye therapeutic post-surgery. The methods and instruments of the present invention may also be used by those in the ophthalmic industry to formulate and test ophthalmic products.

The present invention is directed to methods and devices for use in evaluating the tear film and to use such information to diagnose ophthalmic formula treatment of ocular disease conditions such as dry eye or post-surgical ophthalmic formula treatment and diagnosis. Embodiments of the invention relate to methods and devices for measuring eye blinks and thin layers in a mammalian eye, before and following ophthalmic formula application onto the ocular surface. The methods and devices measure the tear film lipid and aqueous layers as well as blink frequency and maximum interblink interval before and following application of an ophthalmic formula.

FIG. 1 provides a schematic view of the utility of the present invention. With one device, the practitioner will be able to determine if a patient is a candidate for refractive surgery such as PRK, lasik and cataract surgery. The practitioner will be able to diagnose dry eye, and whether it is caused by an aqueous or lipid deficiency. This diagnosis may also be performed on patients subsequent to their refractive surgery. The practitioner will be able to recommend ophthalmic formulas which are best suited for treating needs of the patient with dry eye. The practitioner will also be able to use an instrument according to the present invention to determine if a patient is a candidate for contact lenses and, if so, the type of ophthalmic products which are most suitable for that patient. The methods and instruments of the present invention may also be used by those in the ophthalmic industry to formulate and test ophthalmic products.

The present inventors have surprisingly measured a reduction in thickness in comparison to baseline of the aqueous+lipid layer in the tear film following application of an 0.1% or 0.3% hyaluronic acid (mwt 600 kD-1200 kD) ophthalmic formula. Observation and measurement of a reduction in the thickness of the aqueous+lipid tear film following ophthalmic formula application is important as it allows one to measure for the first time an important change in the tear film which likely correlates to ocular surface health status, subjective comfort, optimization of ophthalmic dosage forms and drug delivery. This discovery is contrary to previously-held beliefs about the tear film.

Conventionally, it has been understood that topical ocular application of an ophthalmic formula designed to supplement the aqueous layer of the tear film will not thin that same layer. It has been believed that topical application of an ophthalmic formula designed to supplement the tear film will only thicken and thus stabilize the tear film. The work of Creech et al. (Creech J L, Do L T, Fatt I, Radke C J. In vivo tear-film thickness determination and implications for tear film stability. *Curr Eye Res* 1998; 17:1058-1066) discloses that as the tear film break-up time increases, tear film thickness theoretically increases. Thus a thinner film would be less stable, which is a long-held belief. In connection with this theoretical relationship, others have shown, for example, that topical application of 0.1% or 0.3% hyaluronic acid (mwt 600 kD-1200 kD) ophthalmic formulas will increase tear film break-up time (TBUT). Therefore, it has long been assumed that an ophthalmic formula that enhances TBUT, thickens the tear film.

As described in more detail below, the present invention provides methods for the observation and measurement of a reduction in thickness in comparison to baseline of the tear film following ophthalmic formula topical application directly onto the ocular surface. This aspect of the invention will improve the diagnosis of dry eye disease treatment and the development of ophthalmic formula therapeutics to treat dry eye and other diseases. Methods for measuring a reduction in thickness of the tear film of an eye, in comparison to baseline, following topical application of an ophthalmic formula, generally comprise the steps of: (a) employing an optical interferometer to measure tear film thickness; (b) topically applying an ophthalmic formula; (c) waiting a period of time; and (d) employing an optical interferometer to measure tear film thickness, wherein the optical interferometer is preferably a wavelength-dependent interferometer. The accuracy of the present invention allows the apparatus to measure tear film thickness as only the aqueous layer, only the lipid layer, the combined aqueous+lipid layer, or all three.

When the dry eye analysis is being performed, the patient is generally not wearing any lenses to correct vision.

As described in more detail below, the present invention provides methods for the measurement of tear production. In the diagnosis of dry eye, this aspect of the present invention may be substituted for the prior art Schirmer and Phenol red thread tests. The method of the present invention for the measurement of tear production generally comprises the sequential steps of measuring baseline tear film thickness with an interferometer, instilling an eye drop, measuring tear film thickness until a time T1 when tear film thickness first returns to baseline, and measuring tear film thickness until a time T2 when tear film thickness returns to baseline for a second time after thinning below baseline. As described herein, the inventors describe this as measuring the rate of tear production. Depending on the depth or level of information gathered, such measurement may be an actual measurement of production or a relative measurement. An example of a relative measurement would be a characterization of a subject as having low tear production, average tear production or high tear production.

Using the above methods, the present invention also allows for the evaluation of in-vivo ocular surface adherence and adhesion of topically-applied molecules such as ophthalmic demulcents and polymers.

As described in more detail below, the present invention provides methods for the measurement of blink frequency and maximum interblink interval. Such methods are simpler, more accurate and precise than prior art video-based methods. The methods of the present invention for measuring blink frequency and maximum interblink interval in an eye generally comprise the sequential steps of projecting at least one wavelength of light from an interferometer onto the ocular surface, measuring light reflectance from the eye over a period of time, wherein said period of time is comprised of sequential time increments and wherein said time increments are smaller than the time wherein the upper lid intersects the light from said interferometer and wherein said measuring occurs over each time increment; and analyzing light reflectance vs. time, wherein said analyzing comprises the determination of number of reductions of light reflectance in a time interval.

As described in more detail below, the present invention provides methods to quantify duration of blurring of vision, especially following ophthalmic formula application. Generally, the method of measuring duration of blurring of vision following ophthalmic formula application comprises the steps of measuring either or both blink frequency and maximum inter-blink interval before ophthalmic formula application, applying said ophthalmic formula to an eye, and sequentially measuring either or both blink frequency and maximum inter-blink interval until such time that either or both blink frequency and maximum inter-blink interval return to their values prior to application of said ophthalmic formula.

Analysis of blink frequency and maximum inter-blink interval net blink measurements according to the present invention may also be used as surrogate measures of ocular comfort. This is highly beneficial to the practitioner, as it provides an analytical measure for something which is typically quite subjective.

The present invention also provides the discovery that simultaneous measurements of tear film aqueous thickness, aqueous+lipid layer thickness, lipid layer thickness, blink frequency and maximum inter-blink interval can be made, before or after application of an ophthalmic formula, to diagnose dry eye and the treatment of dry eye with an ophthalmic formula.

Wavelength-dependent Interferometers of the present invention require a spectrophotometer with a CCD detector and a computer and computer software, all of which provides for fast data acquisition, storage and management. Moreover, the system needs to be capable of accurately measuring the very low light intensity which is reflected from the eye. Large or small spectrophotometers are suitable, although large spectrophotometers are not suitable for routine clinical practice outside the clinical research setting. Smaller spectrophotometers and associated CCD detectors, such as those utilized in interferometer models F20-NIR (950-1700 nm wavelength range, 512-element InGaAs array) and F20-EXR (400-1700 nm wavelength range, 512-element Si & InGaAs arrays) from Filmetrics, Inc. (San Diego, Calif.) are suitable. Also suitable are the DSR-C512 (range 280-1700 nm) and NIRX-SR (range 900-2200 nm) wavelength-dependent optical interferometers from StellarNet (Tampa, Fl).

Other types of optical interferometers may be employed in the present invention. Suitable instrument types which can quantitatively measure thin film thickness, are disclosed in Optical Interferometry, Second Ed. P. Harihan ed. 2003 Elsevier Science, which is incorporated herein in its entirety by reference. The device taught herein should not be confused with a tear scope, which is fundamentally different.

A wavefront device can be used alternatively or in addition to the interferometer of the present invention.

One embodiment of the methods of the present invention employs a wavelength-dependent optical interferometer essentially optically-equivalent to those represented in the aforementioned references, wherein the optical eye-alignment system of the instrument in the *IOVS*, October 2000 reference is used along with the remaining optical system of the instrument in *IOVS*, January 2003 reference. An improved Chromex 500 is spectrophotometer with an Andor CCD detector, Dell computer and Andor software is used in this embodiment of an interferometer of the present invention. Tear film aqueous+lipid, lipid and aqueous layer thicknesses can be measured with this instrument. Thickness-calculation software based upon Statistica 7 from StatSoft® (Tulsa, Okla.) utilized a non-linear estimation method using the Levenburg-Marquardt algorithm applied to the polynomial:

$$v2 = -a - b*v1 - c*(v1)^2 + d[1 + (e/2d)\cos((4\pi n_d \cos\Theta*g/v1) + h)]\mathrm{Exp}(-j/(v1)^2);$$

where $v2$=measured reflectance, $v1$=wavelength, $d=R_0=$(Rmax+Rmin)/2 where R=reflectance, $e/2d$=amplitude=(Rmax−Rmin)/(Rmax+Rmin), $n_d$=refractive index of film, $g$=thickness of the aqueous+lipid layer, $h$=phase, the a, b and c terms represent a $2^{nd}$ order polynomial used to fit the raw data to the large slope oscillation caused by the lipid layer and the $\mathrm{Exp}(-j/(v1)^2)$ term corrects for the modulation of fringe amplitude with wavelength. $\Theta$ is the maximum angle from normal for light incidence on the film, 9.37°. This equation can also be used to measure the thickness of the lipid layer.

Thickness-calculation software based upon Statistica 7 utilizing the Levenburg-Marquardt algorithm applied to the following polynomial is also used to measure the lipid-only layer:

$$v2 = d[1 + (e/2d)\cos((4\pi n_d \cos\Theta*g/v1) + h)];$$

where $v2$=measured reflectance, $v1$=wavelength, $d=R_0=$(Rmax+Rmin)/2 where R=reflectance, $e/2d$=amplitude=(Rmax−Rmin)/(Rmax+Rmin), $n_d$=refractive index of film, $g$=thickness of the lipid layer, $h$=phase and again $\Theta$ is the maximum angle from normal for light incidence on the film. Aqueous-only layer thickness is calculated by subtracting the measured lipid-only layer thickness from the combined aqueous+lipid layer thickness.

A thickness measurement standard curve was employed using NIST-calibrated thin film thickness standards made from vapor-deposited SiO2 on silicon wafers (FIG. 2). Combined instrument and software average error (n=7) with the thickest available standard at 1010.4 nm was 21.0 nm. After standard curve correction, error was −1.2 nm. Absolute errors were similar for all standards. Precision error was 0.13% for the 1010.4 nm standard and 0.05% for the 727.57 nm standard. The standard curve was linear, where y (meas, nm)=1.0081×(actual, nm)+14.024, r2=0.9998. Given that thicker films produce more interference fringes, error decreased with increasing thickness. Thus, aqueous-only and aqueous+lipid tear film thickness errors are expected to be <1% (e.g., <30 nm at 3000 nm (3.00 microns)). Thickness calculations using the above software are applied to the standard curve for final correction.

The interferometer that was assembled by the present inventor has been shown to accurately and precisely measure thin films to less than 50 nm. It utilizes a Chromex 500 is spectrometer with an Andor CCD detector, Dell computer, Andor operating system software and a wavelength range of either 460-1085 nm or 550-1085 nm, and is limited with the present optics to measuring a single spot on the eye, at the central corneal apex, 12.5×133 microns. This spot is produced by projecting light through a 400 micron round aperture and several focusing lenses. This system can be re-configured with suitable optics to measure multiple spots on the ocular surface. By way of example, and not of limitation, the source light can be passed through multiple vertically-aligned slits, all of which are then focused onto the ocular surface in the same vertical orientation. Each individual slit image is then reflected back into the spectrometer. This system can acquire a single spectrum of the tear film in 42 milliseconds or less and can produce excellent accuracy and precision for thickness measurements with data acquisition over a time interval range of milliseconds to continuous measurements up to several hours or more. This allows the kinetic measurement of layer thickness over time, thus allowing the calculation of layer thinning or thickening rates. It also allows for the measurement of blinks and the determination of blink frequency and maximum interblink interval.

Generally, shorter wavelength ranges of 460-1085 nm, 550-1085 nm, or 550-1100 nm are acceptable for measuring tear film aqueous, combined tear film aqueous+lipid layer thicknesses and lipid layer thicknesses, based upon the relatively large thicknesses of these layers in relationship to the wavelengths of light within these aforementioned ranges and the number of interference fringes produced. 400 nm is the preferred cutoff at the lower limit of the wavelength range since this represents the lowest wavelength of visible light. In some cases, however, it may be advantageous to use a lower wavelength limit of 350 nm, to achieve greater accuracy and precision in measuring very thin lipid films at <30 nm thickness. Wavelengths below 400 nm are considered ultraviolet (UV) radiation.

Embodiments of the invention are also directed to wavelength-dependent interferometers with wavelength ranges preferable for measuring thin films or layers less than 200 nm in the eye. Tear film lipid layers are typically 30-200 nm thick, whereas tear aqueous layers are typically greater than 1 and less than 20-30 microns thick, depending upon whether an ophthalmic formula eye drop has been instilled into the eye to produce, at least transiently, an increased tear film aqueous layer beyond the normal highest non-supplemented aqueous thickness of about 5 microns. The wavelength-dependent interferometers of the present invention can measure thin lipid and aqueous films (layers) in the eye and can simultaneously measure thin lipid and aqueous films and combined lipid and aqueous films and corneal epithelial thickness in the eye. Accurate and precise lipid layer measurement is achieved preferably by the use of longer wavelength ranges, e.g., greater than 800 nm in width, within a wavelength range from 350 to 2200 nm Preferably, an upper wavelength value of either 1700 nm or 2200 nm is used along with a wavelength range greater than 800 nm. The wavelength-dependent interferometers of the present invention can also measure layer thickness over time and thus can determine a thinner tear film layer at a particular time interval or kinetic thinning or thickening rate measurements. They can also measure blinks simultaneously with thickness measurements. This measurement assists with the diagnosis of dry eye and the analysis of the outcome of dry eye therapy or therapy for other ocular diseases. As may be evident, the precision of the present invention, which takes measurements without impacting the tear film, has advantages over current diagnostic tools and methods for ocular disease conditions such as dry eye. The methods and interferometers of the present invention can be utilized for dry eye diagnosis, ophthalmic formula development, optimization of ophthalmic dosage forms, optimization of drug delivery, evaluation of therapeutic treatment of ocular disease and improvement of therapeutic treatment and ocular comfort for the subject with dry eye or the subject who has had LASIK or cataract surgery.

Single or multiple spots of light can be focused on the tear film for measurements. Spots are produced by shining the light source through an aperture for a round spot or a slit for a rectangular spot. Spot size on the eye is produced from about 50 to about 400 um diameter round or about 25×50 to about 100×1000 um rectangular slits. Several such round or rectangular spots can be employed. Where multiple spots are desired, multiple apertures or slits can be employed.

Light sources employing voltage and current-regulated power supplies and Tungsten-halogen bulbs can be used to produce light of the desired wavelength ranges and safety. Other types of bulbs can also be employed. The relevant bulb parameters are wavelength and luminosity output, filament and bulb size, power and heat dissipation requirements and bulb lifetime. A variety of suitable bulbs can be found on donsbulbs.com. Examples include the EDW/6V/108W microscope bulb, which has a straight ribbon filament. Bulbs with straight ribbon filaments have the advantage that the image of the light source on the surface of the eye and the surface of the spectrophotometer CCD array can be more focused and intense than that of a coiled filament. This is because a straight ribbon filament presents a single focal plane in the direction of the optical light path as opposed to a coiled filament which has sections of coil nearer and further away from a focusing lens. An optical system employing a ribbon filament bulb will produce photons of greater coherency, maximizing the signal to noise ratio of reflected light. Another example of a suitable bulb is the Avantes Avalight-HAL/HL-60005 tungsten halogen bulb, which produces a wavelength range of 360-1700 nm Other light sources can be used, which produce light wavelengths outside of the desired range. In this case, the desired wavelength range can be produced using light filters in conjunction with such bulbs. For example, if a light source produces wavelengths below 400 nm in the UV range, the UV radiation can be blocked with a filter such a Schott GG435 longpass glass color filter, which blocks light below 390 nm. This filter is available from Edmund Optics in Barrington, N.J. as Edmund part no. G32-752. Filters can be placed just in front of the light source, just in front of the eye and any place in-between. Filter placement just in front of the light source is preferred, at a location where light enters a fiber-optic or optical component conduit (guide), so that only filtered light enters the conduit.

Embodiments of the present invention also include wavelength-dependent interferometers with fiber-optic or short-path optical conduits (guides) to achieve a compact size suitable for routine clinical use. Fiber-optic optical conduits have the added advantage of preventing external light from adding noise to the background signal and thus can enhance the measurement signal and instrument sensitivity. Light is transmitted to the eye and the reflected light is returned to a spectrophotometer in the wavelength-dependent interferometers of the present invention. Fiber optics (e.g., non-coaxial and co-axial fibers, fibers that transmit the desired light radiation wavelength range and fibers that block undesired UV or long-wavelength IR radiation outside of the desired light radiation wavelength range) and short-path optics employing non-fiber-optic optical components separated by space are used to transmit the light radiation to the eye and return the reflected radiation back to a spectrophotometer. Short-path is defined herein as the maximum total optical free-space path measured between any two optical elements of less than 37 cm.

Fiber optic light conduits (guides) such as those from Edmund Optics can be employed in fiber optic-based systems. High transmission glass fiber bundles such as Edmund part nos. G40-639 or J38-659 (Edmund catalog NO78C) are preferred, which have broad light wavelength transmission from about 400 nm to 1800 nm. Fiber optic light guides are often constructed with individual fibers packed in a hexagonal close-packed array. The outermost ring of fibers can be used to either transmit light to the eye or transmit light from the eye to the spectrophotometer. The remaining fibers can be used to transmit light in the alternate light path in the opposite direction, that is, one group of fibers can be used to transmit light to the eye and the other group of fibers can be used to transmit light from the eye back to the spectrophotometer. In this case a separation in the total fiber bundle is employed to physically separate the two groups of bundles so that they can be physically connected to their respective components, such as the spectrophotometer or the light source.

Glass fibers have the added advantage that they do not transmit UV or far IR light radiation, and thus in some embodiments of the present invention, the glass fibers themselves can serve as the UV and/or IR wavelength filter. Other materials can be used in the fiber guides, as is well-known in the art. Fibers which transmit multiple spots of light to the tear film and collect the reflected light from these spots can also be employed. Standard components for coupling fiber optic guides to other parts of the interferometer can be used and are well-known in the art.

Short-path optical conduits employing non-fiber-optic optical components separated by space are used in some embodiments of the present invention to transmit the light radiation to the eye and return the reflected radiation back to a spectrophotometer. Common optical components such as lenses, slits, beam splitters, apertures, mirrors, prisms and polarizers can be used. Two and three element achromatic lenses are preferred lenses, as they correct for on-axis spherical and chromatic aberrations, thus yielding better image quality. One key optical design criterion is to avoid the use of thin films in the optical paths, whether fiber optic or other optical components are used. This eliminates the production of background spectral oscillations arising from the optical system of the interferometer. Where more than one glass beam splitters are employed, the thicknesses should ideally be different, e.g., one 2 mm thick and the other 3 mm thick, again to avoid the possible production of background spectral oscillations which may arise for example from two nearly identical 2 mm thick beam splitters. In other words, when 2 or more reflective beam splitters are used with a thickness difference which falls within the thickness measurement capability of the instrument, this may cause background spectral oscillations. This is normally not an issue with lenses that transmit light. The point is to avoid the creation of an artificial thin film from the combination of optical elements within the system. Any such problem can be detected and corrected in the construction of the instrument, however.

The period of time that one waits after topical formula application before taking measurements can be a few seconds to 24 hours. Generally, a baseline measurement of tear film layer thickness is made, followed by a series of measurements separated by periods of time ranging from a few seconds to minutes to hours. Where the ophthalmic formula is an artificial tear formula, the series of measurements is generally spaced a few minutes apart in the first 30 minutes after topical application of the formula to the ocular surface, and thereafter a series of measurements is taken over successively longer time periods, typically tens of minutes to ½ hours or longer apart. This time may be reduced by comparing data taken during a shorter time period with a standardized graph, chart or data which has been developed based on an analysis of a larger patient group.

While not wanting to be bound by theory, the observation and measurement of a thinner tear film following ophthalmic formula topical application directly onto the ocular surface may be a manifestation of ocular surface adsorption and adherence of ophthalmic demulcent molecules and polymers. Such molecules and polymers are designed to treat dry eye disease.

The methods of the present invention can be utilized to measure the effects on tear film thickness of a topically applied ophthalmic formula, particularly where the ophthalmic formula comprises an ophthalmic demulcent. When the present invention is used in this manner, it may be a tool which may be used to assist in formulating an ophthalmic formula. By way of example, the ophthalmic demulcent can be selected from the group consisting of: carboxymethylcellulose sodium, hydroxyethyl cellulose, hydroxypropyl methylcellulose, methylcellulose, Dextran 70, Gelatin, glycerin, polyethylene glycol 300, polyethylene glycol 400, Polysorbate 80, propylene glycol, polyvinyl alcohol and Povidone.

The ophthalmic formula may also comprise a polymer which is not classified as a USFDA ophthalmic demulcent. The polymer may be selected from the group consisting of anionic, neutral and cationic viscosity polymers. The viscosity polymer may be a viscoelastic polymer such as hyaluronic acid or sodium hyaluronate. The viscosity polymer can be selected from the group comprising hyaluronic acid, hydroxypropyl guar, tamarind seed polysaccharide, and other plant-derived polymers.

Polymers such as the following polyanionic components may be included in the ophthalmic formulas used or formulated in association with the present invention: anionic cellulose derivatives, anionic acrylic acid-containing polymers, anionic methacrylic acid-containing polymers, anionic amino acid-containing polymers and mixtures thereof. A suitable class of polyanionic components are one or more polymeric materials having multiple anionic charges. Examples include, but are not limited to: metal carboxy methylcelluloses, metal carboxy methylhydroxyethylcelluloses, metal carboxy methylstarchs, metal carboxy methylhydroxyethylstarchs, hydrolyzed polyacrylamides and polyacrylonitriles, heparin, glucoaminoglycans, chondroitin sulfate, dermatan sulfate, peptides and polypeptides, alginic acid, metal alginates, homopolymers and copolymers of one or more of: acrylic and methacrylic acids, metal acrylates and methacrylates, vinylsulfonic acid, metal vinylsulfonate amino acids, such as aspartic acid, glutamic acid and the like, metal salts of amino acids, p-styrenesulfonic acid, metal p-styrenesulfonate, 2-methacryloyloxyethylsulfonic acids, metal 2-methacryloyloxethylsulfonates, 3-methacryloyloxy-2-hydroxypropylsulonic acids, metal 3-methacryloyloxy-2-hydroxypropylsulfonates, 2-acrylamido-2-methylpropanesulfonic acids, metal 2-acrylamido-2-methylpropanesulfonates, allylsulfonic acid, metal allylsulfonate and the like.

Among the polypeptides which may be included in the ophthalmic formulas of the present invention, are galectins and mucins, which include those which are naturally present in the tear film of humans. Galectins include those disclosed in U.S. Pat. No. 7,189,697 B2, which is incorporated herein in its entirety by reference.

One of ordinary skill in the art will be able to see that concepts similar to those disclosed herein may be used to measure the flap which is cut in association with refractive surgery.

Example 1

In this example, the combined aqueous+lipid layers tear film thickness was measured in the right eye of a subject (Subj 20, B2W1) prior to the application of Systane drops. The aqueous+lipid layers combined thickness was measured with a wavelength-dependent optical interferometer of the type disclosed in King-Smith, P E et al. The Thickness of the Human Precorneal Tear Film: Evidence from Reflection Spectra. Invest. Ophthalmol. Vis. Sci. 2000 October; 41(11): 3348-3359, which is incorporated herein by reference in its entirety. 50 measurements were taken of the tear film at a 12.5×133 urn spot at the apex of the cornea, each 504 msec, over a 25.2 second interval, to yield a baseline pre-eye drop combined aqueous+lipid layers tear film thickness of 2.03±0.49 microns. Thereafter, a single 40 uL drop of Systane drops, lot 62314F, exp 11/07 (Alcon Laboratories, Fort Worth, Tex.), was instilled into the right eye of the same subject and the combined aqueous+lipid layers thickness was measured several times over a period of 1 hour. It can be seen in FIG. 3 that the instillation of the ophthalmic formula eye drop thickened the tear film over a period of time. Although general thickening of the tear film following topical application of an ophthalmic formula is conventionally expected from the prior art, it is surprising that measurement of tear film thickness at a single spot on the ocular surface yields a smoothly decaying functional relationship between thickness and time. This relationship is interpreted as providing the surprising discovery that these single spot measurements are adequately representative of retention of the instilled fluid volume.

Example 2

In this example, the combined aqueous+lipid layers tear film thickness was measured in the right eye of a subject (Subj 12, B2W1) prior to the application of Systane drops. The aqueous+lipid layers combined thickness was measured using the instrument of example 1, to yield a baseline pre-eye drop combined aqueous+lipid layers tear film thickness of 2.99±0.15 microns. Thereafter, a single 40 uL drop of Alcon® Systane drops, lot 62314F, exp 11/07 (Fort Worth, Tex.), was instilled into the right eye of the same subject and the combined aqueous+lipid layers thickness was measured several times over a period of 1 hour, as indicated in Table 1.

TABLE 1

| time, min | 0 | 0.88 | 2.75 | 5.92 | 9.07 | 12.87 | 15.05 | 19.93 | 31.12 | 60.55 |
|---|---|---|---|---|---|---|---|---|---|---|
| thickness, microns | 2.99 | 10.21 | 5.03 | 3.35 | 2.75 | 2.59 | 2.48 | 2.25 | 2.27 | 1.96 |
| std dev, microns | 0.15 | 0.53 | 0.29 | 0.24 | 0.17 | 0.19 | 0.16 | 0.23 | 0.17 | 0.22 |
|  | rtbaseline |  |  |  | $p < 10e-6$ | $p < 10e-6$ | $p < 10e-6$ | $p < 10e-6$ | $p < 10e-6$ | $p < 10e-6$ |

Figure 4:
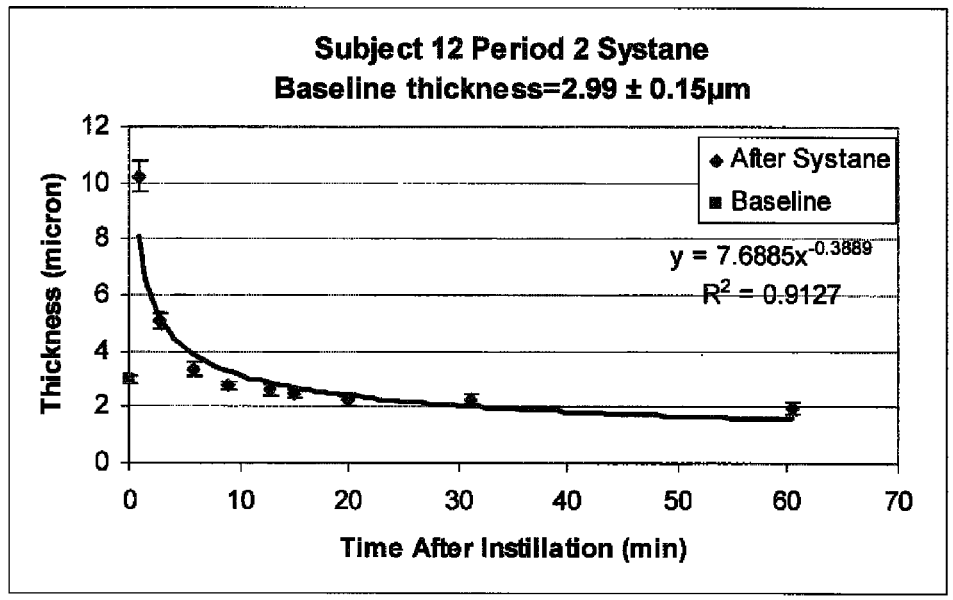
FIG. 4 provides a graph showing a plot of thickness versus time, illustrating the reduction in thickness of the tear film following instillation of an ophthalmic eye drop.

T-test statistical comparisons were calculated between the baseline thickness and the thickness values at 9.07 minutes and thereafter. A significant difference was found between these values and the baseline thickness, as indicated in Table 1. The results surprisingly indicate that the combined aqueous+lipid layers tear film thickness was thinner than the baseline tear film thickness a short time after the instillation of the Systane eye drop. FIG. 4 illustrates the reduction in thickness of the tear film following instillation of Systane. It has been further discovered herein, that topical ocular application of Systane eye drops results after a short period of time (on average after 28.13 minutes), a thinner tear film in 10 out of 22 subjects in an in-vivo test of the methods of the present invention.

Not wishing to be bound by any particular theory, it is believed that the tear film thins after topical application of Systane eye drops because of the ocular surface adsorption and adhesion of a gel matrix of polyethylene glycol 400 and propylene glycol ophthalmic demulcents along with boric acid and the polymer hydroxypropyl guar. This gel matrix forms a new ocular surface interface with the tear film aqueous layer after a short period of time, on the order of a few minutes, resulting in the establishment of a new equilibrium tear film thickness value. Thus, the methods of the present invention can be used to evaluate in-vivo the ocular surface adherence and adhesion of topically-applied molecules such as ophthalmic demulcents and polymers.

Example 3

Figure 5:
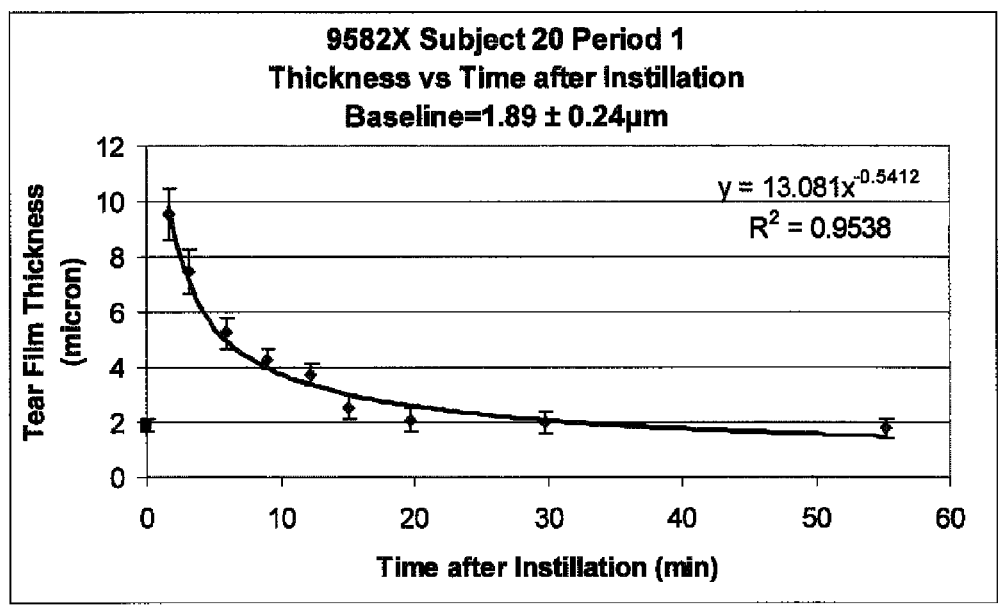
FIG. 5 provides a graph showing a plot of thickness versus time, illustrating an increase in thickness of the tear film following instillation of an ophthalmic eye drop.

In this example, the combined aqueous+lipid layers tear film thickness was measured in the right eye of a subject (Subj 20, B1W1) prior to the application of a commercially available eye drop, Blink® tears lubricating eye drops (Advanced Medical Optics, Inc., Santa Ana, Calif.). The aqueous+lipid layers combined thickness was measured using the instrument of example 1, to yield a baseline pre-eye drop combined aqueous+lipid layers tear film thickness of 1.89±0.24 microns. Thereafter, a single 40 UT, drop of Blink® tears, was instilled into the right eye of the same subject and the combined aqueous+lipid layers thickness was measured several times over a period of 1 hour. It can be seen in FIG. 5 that the instillation of Blink® Tears thickened the tear film over a period of time. Again, although general thickening of the tear film following topical application of an ophthalmic formula is conventionally expected from the prior art, it is surprising that measurement of tear film thickness at a single spot on the ocular surface yields a smoothly decaying functional relationship between thickness and time. The interpretation that these single spot measurements are adequately representative of retention of the instilled fluid volume is reinforced by the comparison of ocular retention time measurements of Blink® Tears (which contains hyaluronic acid), using the methods and devices herein to ocular retention time measurements of hyaluronic acid using a prior art method. The average retention time (e.g., time of first return to baseline thickness) of Blink® Tears using the methods and devices herein in 22 subjects was 39.45±31.65 minutes. This compares to the previously reported value (5 half-life time) of 26.75±12.41 minutes retention time of a 0.2% 4000 kD unpreserved sodium hyaluronate artificial tear solution in buffered saline, measured with gamma scintigraphy (Snibson G R, Greaves J L, Soper N D, Tiffany J M, Wilson C G, Bron A J. Ocular surface residence times of artificial tear solutions. Cornea. 1992 July; 11(4):288-93).

Example 4

Figure 6:
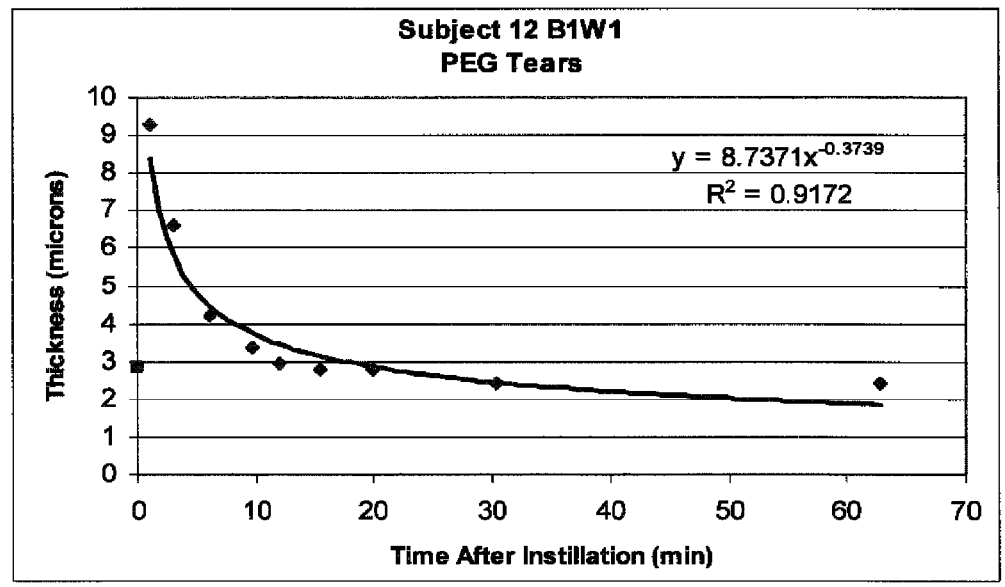
FIG. 6 provides a graph showing a plot of thickness versus time, illustrating how the tear film thinned below baseline following instillation of an ophthalmic eye drop.

In this example, the combined aqueous+lipid layers tear film thickness was measured in the right eye of a subject (Subj 12, B1W1) prior to the application of Blink® Tears. The aqueous+lipid layers combined thickness was measured using the instrument of example 1, to yield a baseline pre-eye drop combined aqueous+lipid layers tear film thickness of 2.83±0.19 microns. Thereafter, a single 40 uL drop of Blink® Tears was instilled into the right eye of the same subject and the combined aqueous+lipid layers thickness was measured several times over a period of 1 hour. It can be seen in FIG. 6 that the instillation of Blink® Tears surprisingly reduced the thickness of the tear film in this subject below the baseline thickness after 20 minutes and that the tear film thickness remained thinner than the baseline thickness for more than an hour. Based on this finding, this subject was believed to have a dry eye with a low tear flow rate, resulting in a slow washout of the instilled eye drop.

Example 5

Figure 7:
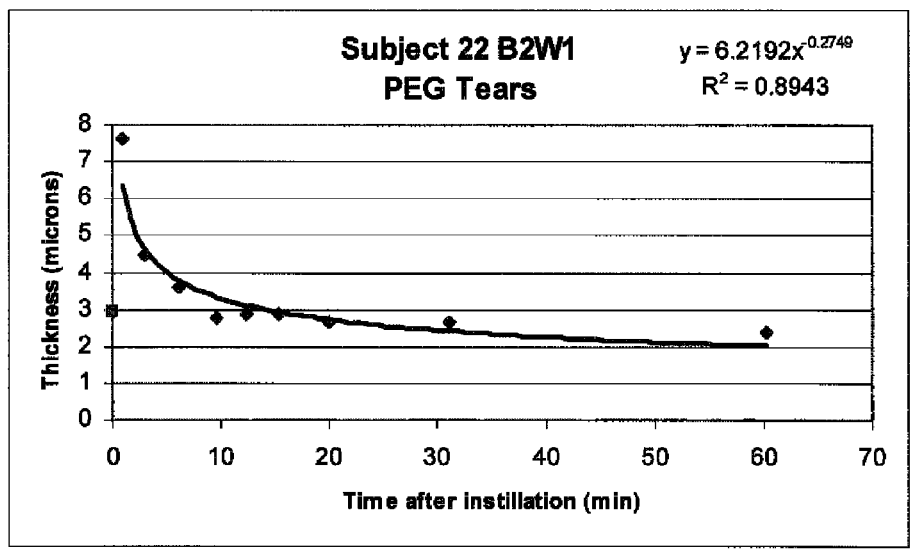
FIG. 7 provides a graph showing a plot of thickness versus time, illustrating how the ophthalmic formula surprisingly reduced the thickness of the tear film below the baseline thickness.

In this example, the combined aqueous+lipid layers tear film thickness was measured in the right eye of a subject (Subj 22, B2W1) prior to the application of an ophthalmic formula eye drop containing 0.20% 800 kD mwt hyaluronic acid. The aqueous+lipid layers combined thickness was measured using the instrument in example 1, to yield a baseline pre-eye drop combined aqueous+lipid layers tear film thickness of 2.93±0.27 microns. Thereafter, a single 40 uL drop of the hyaluronic acid ophthalmic formula, was instilled into the right eye of the same subject and the combined aqueous+lipid layers thickness was measured several times over a period of 1 hour. It can be seen in FIG. 7 that the instillation of the 0.20% 800 kD mwt hyaluronic acid ophthalmic formula surprisingly reduced the thickness of the tear film below the baseline thickness after 15 minutes and that the tear film thickness remained thinner than the baseline thickness for an hour.

Example 6

Figure 8:
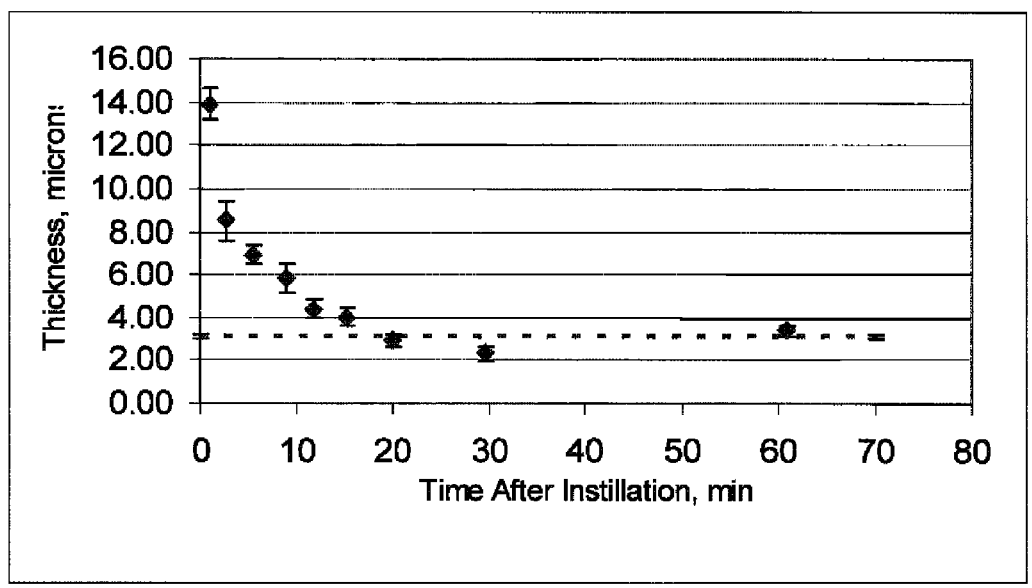
FIG. 8 provides a graph showing a plot of thickness versus time, illustrating that the installation of an ophthalmic formula first thickened the tear film and thereafter the tear film thickness returned to baseline.

In this example, the combined aqueous+lipid layers tear film thickness was measured in the right eye of a subject (Subj 5, B2) prior to the application of an ophthalmic formula eye drop containing 0.20% 800 kD mwt hyaluronic acid. The aqueous+lipid layers combined thickness was measured as in example 1 using the instrument in example 1, to yield a baseline pre-eye drop combined aqueous+lipid layers tear film thickness of 3.12±0.11 microns. Thereafter, a single 40 uL drop of the hyaluronic acid ophthalmic formula, was instilled into the right eye of the same subject and the combined aqueous+lipid layers thickness was measured several times over a period of 1 hour. It can be seen in FIG. 8 that the instillation of the 0.20% 800 kD mwt hyaluronic acid ophthalmic formula first thickened the tear film and thereafter the tear film thickness returned to baseline. This first return to baseline is T1 and occurred at 19.97 minutes, where the tear film was 2.93±0.31 microns thick. Thereafter, the tear film continued to thin and eventually returned to baseline again. This second return to baseline is T2 and occurred at 60.8 minutes, where the tear film thickness was 3.35±0.26 microns thick.

Example 7

Figure 9:
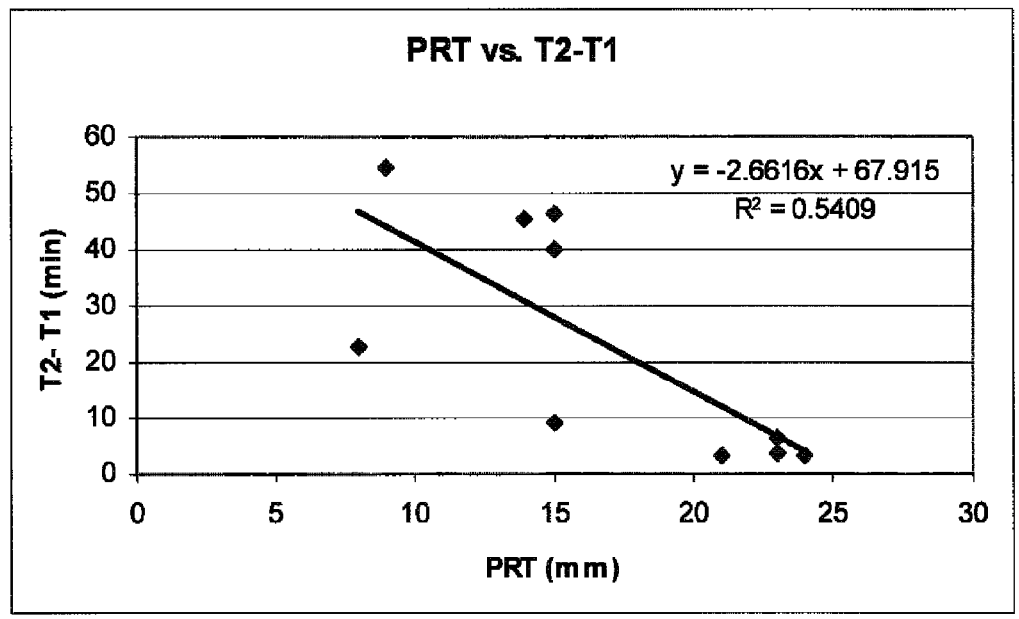
FIG. 9 shows a plot of Phenol Red thread wetting in mm, vs. the difference between T2 and T2 (T2−T1) in minutes.
Figure 10:
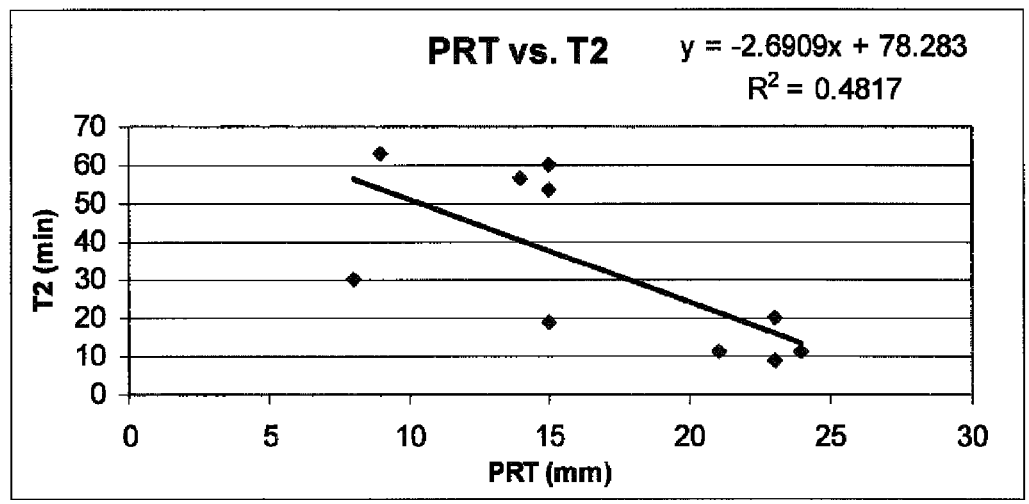
FIG. 10 shows a plot of Phenol Red thread wetting in mm, vs. T2 in minutes.

In this example, the combined aqueous+lipid layers tear film thickness was measured in the right eye of 10 subjects prior to the application of an ophthalmic formula eye drop containing 0.20% 800 kD mwt hyaluronic acid. The aqueous+lipid layers combined thickness was measured as in example 1 using the instrument in example 1. Aqueous tear production was measured using the Phenol Red thread test (PRT). A thread, impregnated with the dye phenol red, was placed into the lower cul-de-sac of each subject's right eye and the amount of wetting of the thread in millimeters in a given time interval was measured. Thereafter, a single 40 uL drop of the hyaluronic acid ophthalmic formula (Advanced Medical Optics, Santa Ana, Calif.), was instilled into the right eye of the same subject and the combined aqueous+lipid layers thickness was measured several times over a period of 1 hour. The instillation of the 0.20% 800 kD mwt hyaluronic acid ophthalmic formula first thickened the tear film and thereafter the tear film thickness returned to baseline. This first return to baseline is T1 and occurred at various times for each individual subject. Thereafter, the tear film continued to thin and eventually returned to baseline again. This second return to baseline is T2 and occurred at various times for each individual subject. The T2–T1 time interval is the time period of tear film thinning below baseline. FIG. 9 shows the plot of PRT wetting in mm, vs. T2–T1 in minutes. FIG. 10 shows a similar plot of PRT wetting in mm vs. T2 in minutes. The figures show downward trends of both T2–T1 and T2 vs. PRT wetting. The time period of tear film thinning below baseline, T2–T1, negatively correlates to PRT wetting. This is because it is believed herein that an individual with high tear production will be able to wash out the residual instilled tear product, still remaining in the T2–T1 period, faster than an individual with low tear production. Thus, the time period T2–T1 or T2 time alone, are proportional to tear production and can be viewed as substitute measures for tear production.

Example 8

In this example, the combined aqueous+lipid layers tear film thickness was measured in the right eye of 6 subjects prior to the application of an ophthalmic formula eye drop containing 0.20% 800 kD mwt hyaluronic acid (10.8 cp tear). The aqueous+lipid layers combined thickness was measured as in example 1 using the instrument in example 1. Aqueous tear production was measured as in example 7 using the Phenol Red thread test (PRT) in the right eye. Tear film breakup time, TBUT, in seconds, was also measured in the same eye. Thereafter, a single 40 uL drop of the hyaluronic acid ophthalmic formula, was instilled into the right eye of the same subject and the combined aqueous+lipid layers thickness was measured several times over a period of 1 hour. The instillation of the 0.20% 800 kD mwt hyaluronic acid ophthalmic formula first thickened the tear film and thereafter the tear film thickness returned to baseline. This first return to baseline, T1, occurred at various times for each individual subject. Thereafter, the tear film continued to thin and eventually returned to baseline again. This second return to baseline, T2, occurred at various times for each individual subject. The combined aqueous+lipid layers tear film thickness was measured in the right eye of a second group of 5 subjects prior to the application of an ophthalmic formula eye drop containing carboxymethylcellulose (Refresh Tears®, Allergan Pharmaceuticals, Irvine, Calif.; 3 cp tear). The aqueous+lipid layers combined thickness was measured as in example 1 using the instrument in example 1. Aqueous tear production was measured as in example 7 using the Phenol Red thread test (PRT) in the right eye. Tear film breakup time, TBUT, in seconds, was also measured in the same eye. Thereafter, a single 40 uL drop of the carboxymethylcellulose ophthalmic formula was instilled into the right eye of the same subject and the combined aqueous+lipid layers thickness was measured several times over a period of 1 hour. The instillation of the carboxymethylcellulose ophthalmic formula first thickened the tear film and thereafter the tear film thickness returned to baseline. This first return to baseline, T1, occurred at various times for each individual subject. Thereafter, the tear film continued to thin and eventually returned to baseline again. This second return to baseline, T2, occurred at various times for each individual subject.

Figure 11:
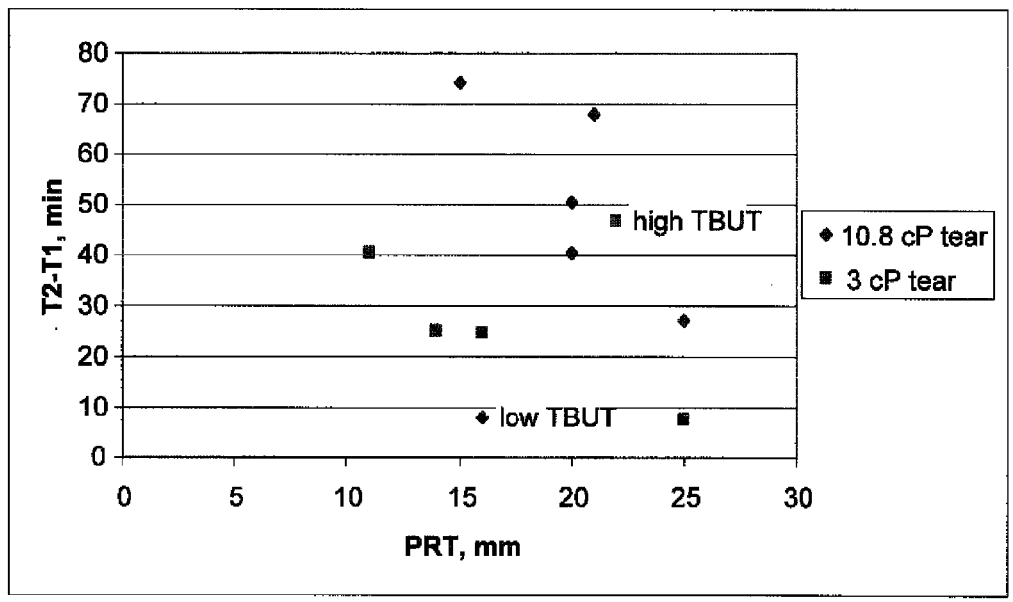
FIG. 11 shows a plot of Phenol Red thread wetting in mm, vs. the difference between T2 and T2 (T2−T1) in minutes for two ophthalmic formulas.
Figure 12:
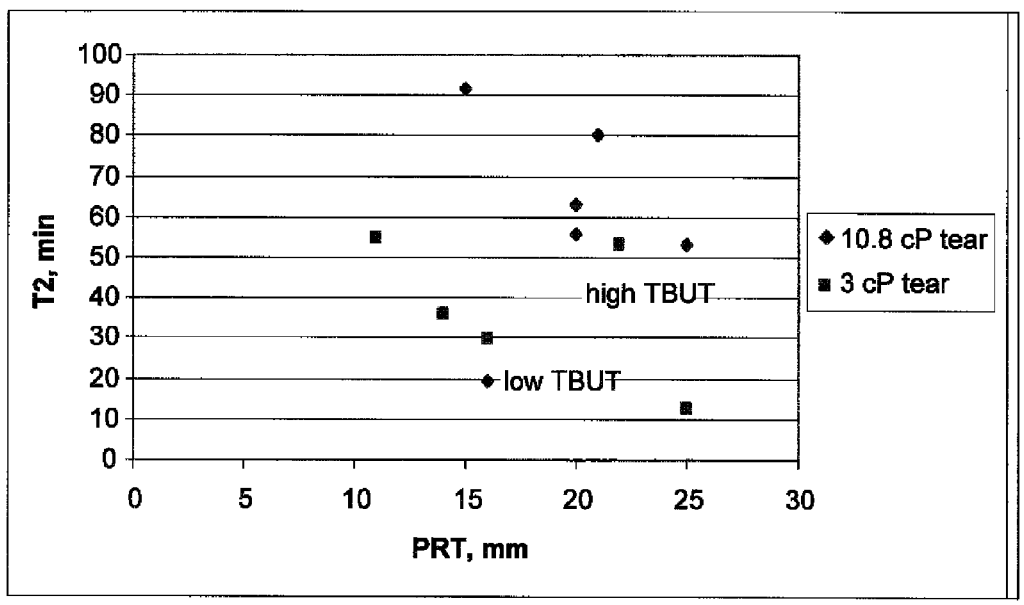
FIG. 12 shows the plots of PRT wetting in mm, vs. T2−T1 in minutes for two ophthalmic formulas.

FIG. 11 shows the plots of PRT wetting in mm, vs. T2–T1 in minutes for both tear formulas. FIG. 12 shows similar plots of PRT wetting in mm vs. T2 in minutes for both tear formulas.

Two subjects, one from each of the tear product groups, are outliers from their respective groups. These subjects had in one case a very low TBUT (6.4 sec) and a very high TBUT (17.7 sec) in the other case. TBUT values averaged 10.9 seconds for both groups. A high TBUT implies a low blink frequency, whereas a low TBUT implies a high blink frequency. The higher the blink frequency, the more rapidly an instilled drop will be washed out of the eye. Thus, the individual with a low TBUT value is expected to have a lower T2–T1 period and lower T2 time than others in the same group. Conversely, the individual with a high TBUT value is expected to have a higher T2–T1 period and higher T2 time than others in the same group. With the exceptions of the two subjects with very low or high TBUT values, the figures show downward trends of both T2–T1 and T2 vs. PRT wetting. The time period of tear film thinning below baseline, T2–T1, negatively correlates to PRT wetting. In this example, the residual instilled lower viscosity 3 cP tear product, still remaining in the T2–T1 period, is washed out faster than the higher viscosity 10.8 cP tear product. Thus, the time period T2–T1 or T2 time alone, are proportional to tear production and can be viewed as substitute measures for tear production.

Measuring T2–T1 or T2 alone to derive a proportional measure of aqueous tear production can be quicker if one uses a 1 cP saline solution instead of a higher viscosity tear formula. One drop of sterile, unit dose, isotonic 0.9% sodium chloride was instilled into the right eyes of four subjects in a separate test, after their baseline tear film thicknesses had been measured. Measured T2/T1 values were 29.92/4.46, 15.25/6.03, 17.07/8.95 and 12.40/7.75 minutes. Thus, it takes about 15 minutes to measure tear production in this manner. A variety of eye drops of differing composition can be used to measure tear production, including saline, buffered saline, and any commercially available eye drop. Saline is preferred.

In summary, the method of the present invention for the measurement of aqueous tear production comprises the sequential steps of measuring baseline tear film thickness with an interferometer, instilling an eye drop, measuring tear film thickness until a time T1 when tear film thickness first returns to baseline, and measuring tear film thickness until a time T2 when tear film thickness returns to baseline for a second time after thinning below baseline. An alternative method of the present invention for the measurement of aqueous tear production comprises the sequential steps of measuring baseline tear film thickness with an interferometer, instilling an eye drop, measuring tear film thickness until a time T1 when tear film thickness first returns to baseline, measuring tear film thickness until a time T2 when tear film thickness returns to baseline for a second time after thinning below baseline, and subtracting T1 from T2.

Example 9

This example illustrates interferometer scan time tests for blink frequency and maximum inter-blink interval determination using wavelength-dependent interferometry with a single light spot at the apex of the cornea. The interferometer instrument of example 1 was used in this example. Blink frequency is the number of blinks in a given time period. Maximum inter-blink interval is the maximum time in seconds between 2 successive blinks. The upper lid during blinking will transit and block the interferometer light spot at the apex of the cornea for a finite, small period of time. During this time period, the light will be absorbed by the outside skin of the upper lid and hence will not return to the spectrometer.

know the upper lid velocity profile across the cornea as well as the palpebral aperture, the distance between the open lids. However, when the scan time is short enough, all subjects can be measured. This scan time can be determined by experiment. An additional unknown factor is that the interferometer signal to noise ratio changes with scan time. In particular, as the scan time decreases, the signal to noise ratio decreases, thus one cannot predict if a particular scan time provides a good ratio for an acceptable spectrum. This also can be determined by experiment. Another unknown factor is the amount of light projected onto the eye, which also affects the signal to noise ratio. If the light output from the light bulb is too low and/or the spot size of the light projected onto the ocular surface too small, not enough light will be reflected from the tear film back into the spectrometer. These factors can be determined by experiment. Table 2 summarizes Chromex 500 is spectrometer parameters of the instrument utilized in example 1 for blink frequency determination. Each spectrum is acquired during a 21 millisecond exposure time. Another 21 milliseconds are required for data accumulation by the computer, for a total of 42 milliseconds. Typically, 2 or more spectra are acquired and added together, to increase the signal to noise ratio. Thus, the total scan time is 84 milliseconds for 2 added spectrum scans and 504 milliseconds for 12 added spectrum scans. A typical data acquisition interval for one subject should be long enough to capture multiple blinks, or from about a few seconds to a few minutes. Preferably, it is about 20-40 seconds. In this example, 25.2 seconds was employed for tests shown in FIGS. 13-16. 21.42 milliseconds was employed for the test shown in FIG. 16. In 25.2 seconds, 50 final spectra were acquired using a 504 millisecond scan time and 300 final spectra can be acquired using an 84 millisecond scan time.

TABLE 2

Chromex 500is Spectrometer parameters for blink frequency determination.

Figure 13:
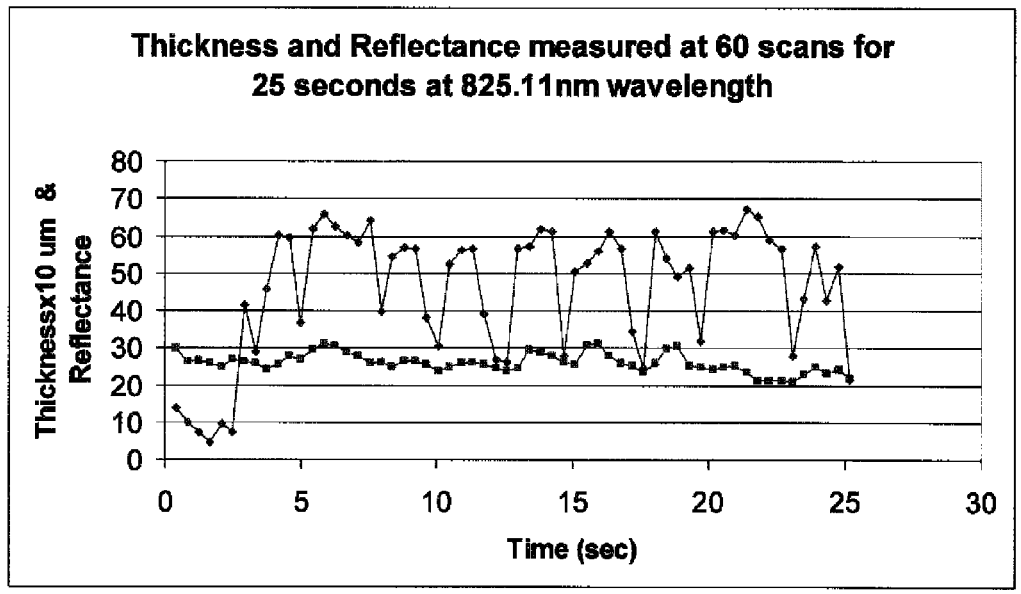
FIG. 13 shows a plot of Phenol Red thread wetting in mm, vs. T2 in minutes for two ophthalmic formulas.
Figure 14:
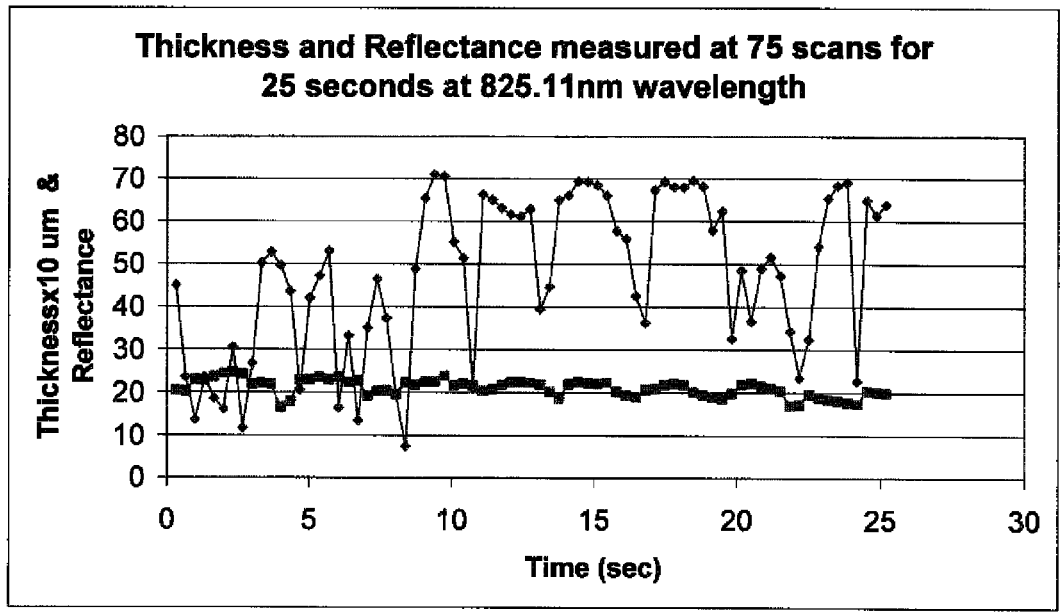
FIGS. 14-16 shows various plots of thickness and reflectance versus time, in seconds, where the figures differ in terms of the number of spectrum scans.
Figure 15:
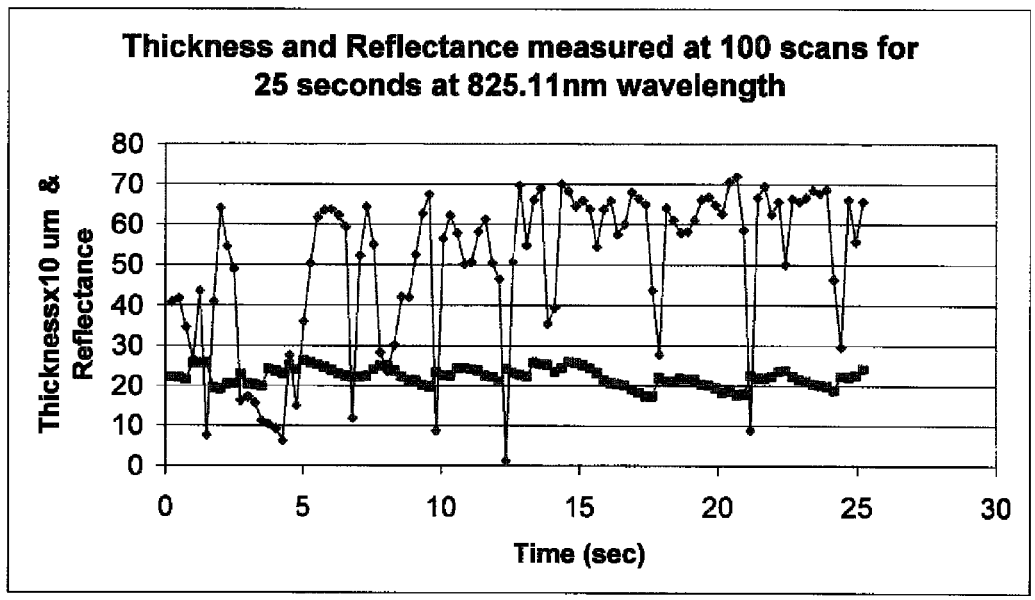
Figure 16:
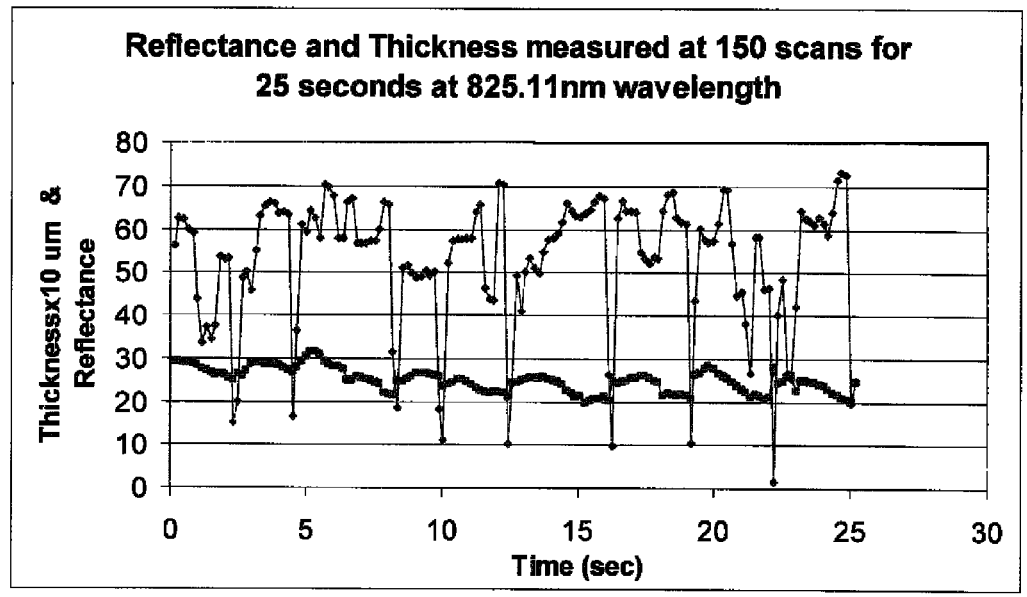

| Corresponding figures | FIG. 16 | FIG. 15 | FIG. 14 | FIG. 13 | FIG. 12 | none |
|---|---|---|---|---|---|---|
| Exposure time (sec)/single spectrum scan | 0.021 | 0.021 | 0.021 | 0.021 | 0.021 | 0.021 |
| Accumulate cycle time (sec) (total time for 1spectrum scan) | 0.042 | 0.042 | 0.042 | 0.042 | 0.042 | 0.042 |
| Number of accumulations (# spectrum scans that are added) | 2 | 4 | 6 | 8 | 10 | 12 |
| Kinetic cycle time (sec) (# added scans × total time/1 scan) | 0.084 | 0.168 | 0.252 | 0.336 | 0.42 | 0.504 |
| Number in Kinetic Series (number of individual final spectra) | 300 | 150 | 100 | 75 | 60 | 50 |
| total run time (sec) | 25.2 | 25.2 | 25.2 | 25.2 | 25.2 | 25.2 |
| Can correctly capture blinks | yes | yes | no | no | no | no |

The amount of light reflection during this time period will drop substantially or to zero or near zero. Thus, by analyzing or plotting light reflectance (amount of light) at a constant wavelength vs. time, one can determine when a blink occurs and therefore both blink frequency and maximum inter-blink interval. Plots of light reflectance vs. time will have downwards-directed spikes or "peaks", each of which corresponds to a single blink. A wavelength at the center of the spectrum range can be selected. It has been determined that wavelength is not critical for blink frequency and maximum inter-blink interval determination. Thus any wavelength that an interferometer employs can be utilized. A narrow band of several wavelengths can also be used, provided optical interference effects do not affect the summed light reflectance. This method for measuring blink frequency and maximum inter-blink interval is only successful when the interferometer scan time, or final spectrum data acquisition time interval, is short enough to capture the rapid movement of the upper lid as it transits the light beam. In principle, one cannot predict what scan time will work for each person, since one would have to FIGS. 13 through 17 show plots of light reflectance vs. time and also tear film thickness vs. time, measured at the same time on the same eye, using the Chromex 500 is spectrometer parameters in Table 2. No figure of reflectance vs. time using a 504 millisecond scan time and associated instrument parameters is shown. It is a useful method of the present invention to analyze or plot tear film thickness vs. time along with reflectance vs. time, as the thickness data can provide additional confirmation of blink occurrence, since tear film thickness increases immediately following a blink. FIG. 13 shows that acquiring 60 final spectrum scans in 25.2 seconds (e.g., a 420 millisecond final spectrum scan time) is too slow to accurately determine blinking. Measured light reflectance does not decrease enough and there is a poor match between decreased reflectance and increased thickness. The same is true for the tests shown in FIGS. 14 and 15, although one can see successive improvements over the test in FIG. 11. The test shown in FIG. 16, where 150 final spectrum scans were acquired in 25.2 seconds (e.g., a 168 millisecond final spectrum scan time) successfully captures all blinks, as does the test shown in FIG. 17, where final spectrum scans were acquired at a rate of 300 in 25.2 milliseconds (e.g., a 84 millisecond final spectrum scan time).

The one data point at time zero on each of the graphs herein showing thickness vs. time represents the baseline tear film thicknesses prior to adding the drops.

Figure 17:
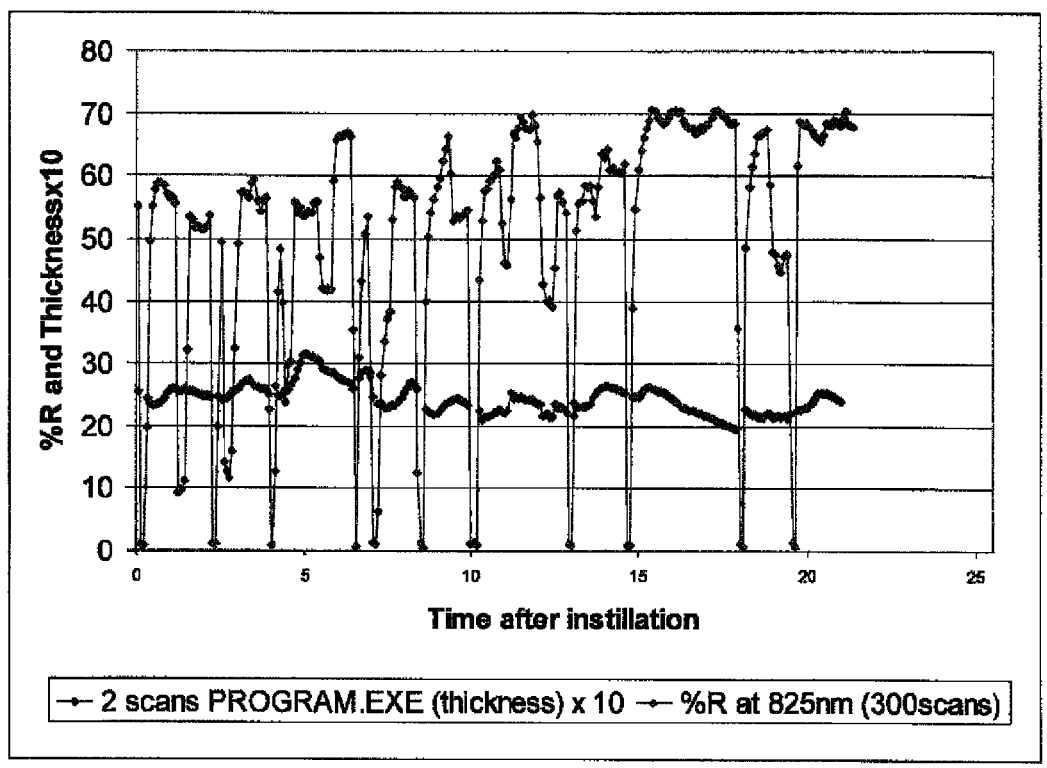
FIG. 17 shows plots of tear thickness (microns×10) vs. time (sec)(flatter line) and % R vs. time (sec)(more variable line) for 300 scans/25.2 sec, 1 scan/0.084 sec; % R vs. time plot shows blinks; 14 major blinks shown.

FIG. 17 also illustrates the maximum inter-blink interval, which occurred between two successive blinks occurring at 14.784 and 18.144 seconds, giving a value of 3.360 seconds. The Chromex 500 is spectrometer used acquires data with millisecond accuracy, resulting in millisecond accuracy for both blink frequency and maximum inter-blink interval determination. It is often useful to measure both blink frequency and maximum inter-blink interval, as they are both known to independently correlate to dry eye status and they have inverse correlations with each other and dry eye status. For example, a high blink frequency, which correlates to dry eye, is accompanied by a short maximum inter-blink interval. Conversely, a long maximum inter-blink interval is accompanied by a low blink frequency among normal subjects without dry eye. The analysis of reflectance vs. time to determine blink frequency or maximum interblink interval can involve plotting and manual peak counting for blink frequency and manual determination of time differences for maximum inter-blink interval or the employment of peak-picking algorithms or computer software using peak-picking algorithms.

Figure 18:
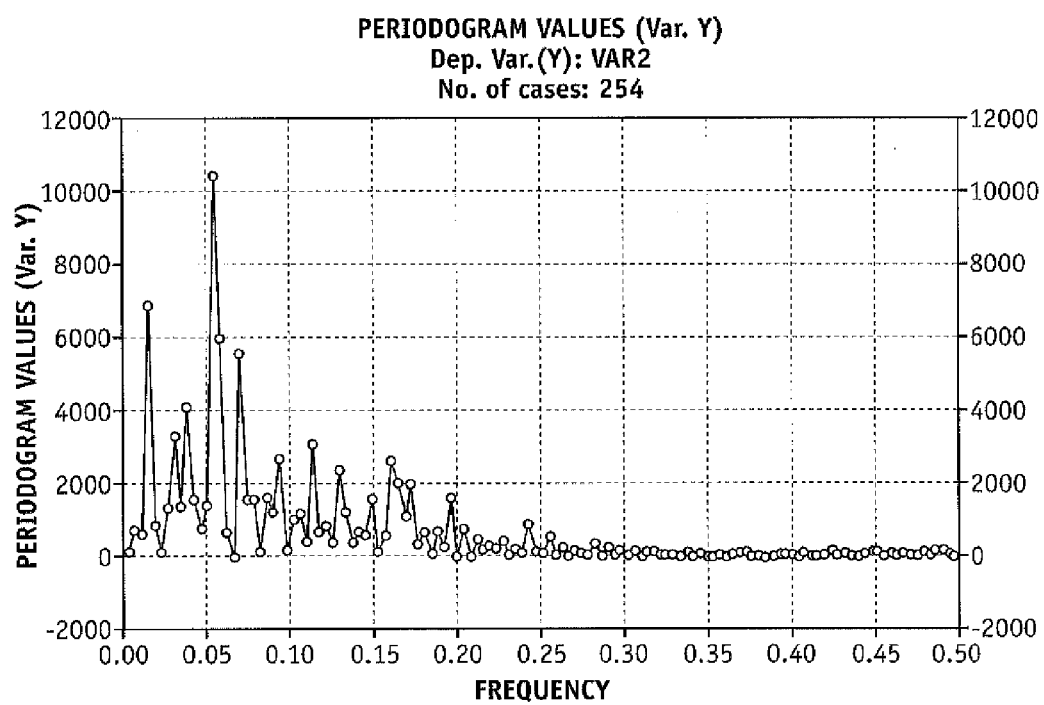
FIG. 18 shows a Fourier-transform-frequency plot of the % reflectance vs. time plot from FIG. 16.

Another useful method of the present invention involves Fourier-transformation (FT) of blink frequency data, to determine the blink frequency spectrum. This is illustrated in FIG. 18, which is a Fourier-transform-frequency plot of the % reflectance vs. time plot from FIG. 17. Since the time increment=0.084 sec, Fourier frequency=blinks/0.084 sec. The maximum Fourier frequency is 0.0551=frequency/0.084 sec=0.656 blinks/sec=1.52 sec/blink. Given the total time interval of 21.42 sec and 1.52 sec/blink, 14.05 blinks occurred. Also, since there are typically several Fourier frequencies, one can apply a proportional weight to each frequency and then sum the values to determine a single weighted frequency term representing blink frequency.

In summary, the method of the present invention for measuring blink frequency in an eye comprises the sequential steps of projecting at least one wavelength of light from an interferometer onto the ocular surface, measuring light reflectance from the eye over a period of time, wherein said period of time is comprised of sequential time increments and wherein said time increments are smaller than the time wherein the upper lid intersects the light from said interferometer and wherein said measuring occurs over each time increment; and analyzing light reflectance vs. time, wherein said analyzing comprises the determination of number of reductions of light reflectance in a time interval.

The method of the present invention for measuring maximum inter-blink interval in an eye comprises the sequential steps of projecting at least one wavelength of light from an interferometer onto the ocular surface, measuring light reflectance from the eye over a period of time, wherein said period of time is comprised of sequential time increments and wherein said time increments are smaller than the time wherein the upper lid intersects the light from said interferometer and wherein said measuring occurs over each time increment; and analyzing light reflectance vs. time, wherein said analyzing comprises the determination of the maximum time interval between reductions of light reflectance.

Given that the methods of the present invention can accurately measure blink frequency and maximum inter-blink interval, it is also possible using these methods to quantify duration of blurring of vision, especially following ophthalmic formula application. This is based upon the known relationship between blurring and blinking. Thus, the method of measuring duration of blurring of vision following ophthalmic formula application comprises the steps of measuring either or both blink frequency and maximum inter-blink interval before ophthalmic formula application, applying said ophthalmic formula to an eye, and sequentially measuring either or both blink frequency and maximum inter-blink interval until such time that either or both blink frequency and maximum inter-blink interval return to their values prior to application of said ophthalmic formula.

Blink frequency and maximum inter-blink interval can also be used as surrogate measures of ocular comfort. The following example illustrates this.

Example 10

In this example, combined aqueous+lipid layer thickness, blink frequency and maximum interblink interval were measured at baseline in the right eye of a subject with dry eyes with poor ocular comfort, prior to the instillation of an artificial tear solution. The methods of example 9 were used, wherein 150 final spectral scans were acquired in 25.2 seconds. Thereafter, a single 40 µL drop of an artificial tear solution was instilled into the subject's right eye and comfort and combined aqueous+lipid layer thickness, blink frequency and maximum interblink interval were assessed and measured after approximately 75 minutes. Table 3 presents the results. One can see the directional correlation between subjective comfort and the measurements of blink frequency and maximum interblink interval. Combined aqueous+lipid layer tear film thickness showed no such directional correlation, although a thickness of 2.34 microns is considerably thinner than the reported thickness of 2.94 microns among normals in one study (King-Smith P, Fink B, Fogt N, Nichols K, Hill R, Wilson G. The Thickness of the Human Precorneal Tear Film: Evidence from Reflection Spectra. *IOVS*, October 2000, Vol. 41, No. 11:3348-3359) and 3.98±1.06 microns in another (Nichols J, Mitchell G, King-Smith P. Thinning rate of the Precorneal and Prelens Tear Films. IOVS, July 2005, Vol. 46, No. 7: 2353-2361). Both studies involved relatively young subjects with an average age of 32 years, however. The number of blinks in the measurement time interval, 25.2 seconds, matches well with the figures of 6.0 blinks/25.2 seconds for normals and 14.2 blinks/25.2 seconds for dry eye subjects reported by Tsubota et al. (IBID). This example illustrates the need on occasion to measure blink parameters in addition to thickness, to make a good diagnosis of dry eye.

TABLE 3

| Parameter | baseline | 75 min |
|---|---|---|
| Time, min | 0.00 | 74.75 |
| Ave. thickness, microns | 2.34 | 2.47 |
| s.d., thickness, microns | 0.30 | 0.43 |
| Comfort (1-5 scale, 5 best) | 1.00 | 5.00 |
| Blinks in 25.2 sec | 16 | 9.5 |
| Max. Interblink Interval, sec | 1.68 | 2.856 |

Example 11

In this example, combined aqueous+lipid layer thickness, lipid layer thickness, comfort and TBUT were measured, as indicated in Table 4, at baseline in the right eye of subjects with dry eyes with poor ocular comfort and subjects with good ocular comfort and no dry eye. The thickness methods of example 1 were used, wherein 50 final spectral scans were acquired in 25.2 seconds, with the exception of subject 4, wherein 150 scans were acquired. Tear film layer thicknesses represent averages of 50 measurements, again with the exception of subject 4, where thicknesses represent averages of 150 scans. Comfort and TBUT were not determined (n.d.) for one and two subjects, respectively. Comfort was rated for all but Subject 4 on a scale of 1-10, with 10 being best and on a scale of 1-5, with 5 being best for Subject 4. Subject H had a very thick aqueous+lipid layer and intermediate lipid layer, which illustrate quantitatively for the first time the tear film thicknesses which heretofore have been only qualitatively known to occur in blepharitis, a condition causing dry eye. Thus, the methods of the present invention to measure tear film aqueous+lipid and lipid layers, to diagnose a condition of dry eye are illustrated. Subject 17 had a thin aqueous+lipid layer, somewhat thin lipid layer, excellent comfort, TBUT>10 seconds and no dry eye. This is an example illustrating the need for additional measurements of blink frequency and/or maximum interblink interval or tear production to make a correct diagnosis of dry eye or normal eye status. Subject 18 had a very thick aqueous+lipid layer and thick lipid layer, excellent comfort and marginal TBUT. Here, a correct diagnosis of normal eye condition can be made on the basis of thickness measurements alone. Subject 4, reviewed in Example 10, had a thin aqueous+lipid layer and normal lipid thickness at baseline. These two measurements alone are insufficient to correctly diagnose the dry eye condition. However, when thickness measurements are combined with blink frequency and maximum interblink interval measurements in example 10, a correct diagnosis of ocular discomfort can be made. Lipid layer thickness for subject 4 at 75 minutes was 111 nm, which corresponds to the high comfort (5), low blink frequency and longer maximum interblink interval measured at this time (Table 3). Subject 13 had a moderately thin aqueous+lipid layer, somewhat thin lipid layer, good comfort and low TBUT. This subject occasionally experiences dry eye. Here, the thickness measurements alone are not quite sufficient to correctly diagnose the dry eye status with respect to subjective comfort, but do correspond to TBUT, an accepted measure of dry eye. Blink measurements would be helpful to diagnose comfort status in subject 13. Subject 8 had a normal aqueous+lipid layer, extremely thick lipid layer, poor comfort and low TBUT. The normal aqueous+lipid layer and extremely thick lipid layer are consistent with a diagnosis of meibomianitis, which leads to excess lipid production and subsequent dry eye. Here again, the thickness measurements alone are sufficient to correctly diagnose the dry eye status.

TABLE 4

| Subject | Aqueous & Lipid (um) | Lipid (nm) | Comfort | TBUT, sec |
|---|---|---|---|---|
| Subj H (blepharitis) | 3.51 | 70 | n.d. | n.d. |
| Subj 17, B1 (thin) | 1.31 | 45 | 9 | 13.1 |
| Subj 18, B2 (thick) | 4.03 | 169 | 9 | 9.3 |
| Subj 4, baseline | 2.34 | 117 | 1 | n.d. |
| Subj 4, 75 min | 2.47 | 111 | 5 | n.d. |
| Subj 13, B2 (thin) | 1.98 | 56 | 8 | 6.6 |
| Subj 8, B2 (thin) | 2.69 | 181 | 4 | 5.7 |

Ideally, multiple measurements of the tear film and eye can be made simultaneously, to obtain a more accurate and specific diagnosis of dry eye. For example, tear film aqueous+lipid layer thickness, lipid layer thickness, aqueous layer thickness, blink frequency and maximum interblink interval can be measured simultaneously prior to or after the instillation of an ophthalmic formula. Measurements of T2 and T1 can be made after instillation of an ophthalmic formula to obtain an assessment of aqueous tear production. Any of these measurements can be made in combination with one another.

What is claimed is:

1. A method of measuring the ocular comfort of a subject, the method comprising:
   projecting a wavelength of light onto an ocular surface;
   measuring light reflectance from the ocular surface over a period of time wherein the period of time is comprised of sequential time increments, and wherein the sequential time increments are smaller than a time when the light reflectance is blocked from being measured; and
   analyzing the light reflectance over the period of time.

2. The method as in claim 1, wherein said analyzing comprises analysis of light reflectance versus time.

3. The method as in claim 1, wherein said analyzing comprises a determination of a number of reductions of light reflectance.

4. The method as in claim 1, wherein said analyzing comprises a determination of a maximum time interval between reductions of light reflectance.

5. The method as in claim 1, wherein the analyzing of light reflectance results in blink frequency data and further comprising the step of performing a fourier transformation on the blink frequency data comprising reductions of light reflectance over time.

6. A method of increasing ocular comfort of a subject, the method comprising:
   projecting a wavelength of light onto an ocular surface;
   measuring light reflectance from the ocular surface over a period of time, wherein the period of time is comprised of sequential time increments, and wherein the sequential time increments are smaller than a time when the light reflectance is blocked from being measured;
   analyzing the light reflectance over the period of time; and
   recommending an ophthalmic solution for use by the subject.

7. The method as in claim 6, wherein said analyzing comprises analysis of light reflectance versus time.

8. The method as in claim 6, wherein said analyzing comprises a determination of a number of reductions of light reflectance.

9. The method as in claim 6, wherein said analyzing comprises a determination of a maximum time interval between reductions of light reflectance.

10. The method as in claim 6, wherein the analyzing of light reflectance results in blink frequency data and further comprising the step of performing a fourier transformation on the blink frequency data comprising reductions of light reflectance over time.

11. The method as in claim 6, wherein the ophthalmic solution contains an ingredient selected from the group consisting of methylcellulose, Dextran 70, Gelatin, glycerin, polyethylene glycol 300, polyethylene glycol 400, Polysorbate 80, propylene glycol, polyvinyl alcohol, povidone, hyaluronic acid, sodium hyaluronate, hydroxypropyl guar, tamarind seed polysaccharide, plant-derived polymers, polymeric materials having multiple anionic charges, anionic cellulose derivatives, anionic acrylic acid-containing polymers, anionic methacrylic acid-containing polymers, anionic amino acid-containing polymers, the salts of any of the foregoing and mixtures thereof.

* * * * *